(12) United States Patent
Osypka

(10) Patent No.: US 8,262,671 B2
(45) Date of Patent: Sep. 11, 2012

(54) VASCULAR INTRODUCER HAVING HEMOSTATIC VALVE WITH INTEGRAL SEAL

(75) Inventor: Thomas P. Osypka, Palm Harbor, FL (US)

(73) Assignee: Oscor Inc., Palm Harbor, FL (US)

( * ) Notice: Subject to any disclaimer, the term of this patent is extended or adjusted under 35 U.S.C. 154(b) by 1166 days.

(21) Appl. No.: 11/941,906

(22) Filed: Nov. 16, 2007

(65) Prior Publication Data

US 2008/0097386 A1    Apr. 24, 2008

Related U.S. Application Data

(63) Continuation-in-part of application No. 10/940,415, filed on Sep. 14, 2004, now Pat. No. 8,137,317, which is a continuation-in-part of application No. 10/389,229, filed on Mar. 14, 2003, now Pat. No. 7,192,433.

(60) Provisional application No. 60/859,310, filed on Nov. 16, 2006, provisional application No. 60/879,499, filed on Jan. 9, 2007.

(51) Int. Cl.
 A61B 17/00    (2006.01)
 A61F 11/00    (2006.01)
 A61M 29/00    (2006.01)
 A61M 5/178    (2006.01)
(52) U.S. Cl. ............. 606/108; 606/1; 606/192; 606/194
(58) Field of Classification Search ................. 604/256, 604/164.01–164.11, 167.01–167.06, 246, 604/264, 160, 161; 606/1, 108, 192, 194
See application file for complete search history.

(56) References Cited

U.S. PATENT DOCUMENTS

| | | | |
|---|---|---|---|
| 4,960,412 A * | 10/1990 | Fink | 604/167.04 |
| 6,159,182 A * | 12/2000 | Davis et al. | 604/167.06 |
| 7,621,894 B2 * | 11/2009 | Leeflang et al. | 604/161 |
| 2005/0267487 A1 * | 12/2005 | Christensen et al. | 606/108 |

* cited by examiner

Primary Examiner — Matthew F Desanto
(74) Attorney, Agent, or Firm — Edwards Wildman Palmer LLP; Scott D. Wofsy

(57) ABSTRACT

A vascular introducer includes a proximal hub portion with an interior bore, an elongated sheath extending distally from the hub portion, with a lumen in communication with the interior bore of the hub portion, and a hemostatic valve disposed within the bore of the hub portion. The hemostatic valve has a passage extending therethrough, and includes a sealing flap movable between an open position relative to the passage and a closed position relative to the passage.

23 Claims, 28 Drawing Sheets

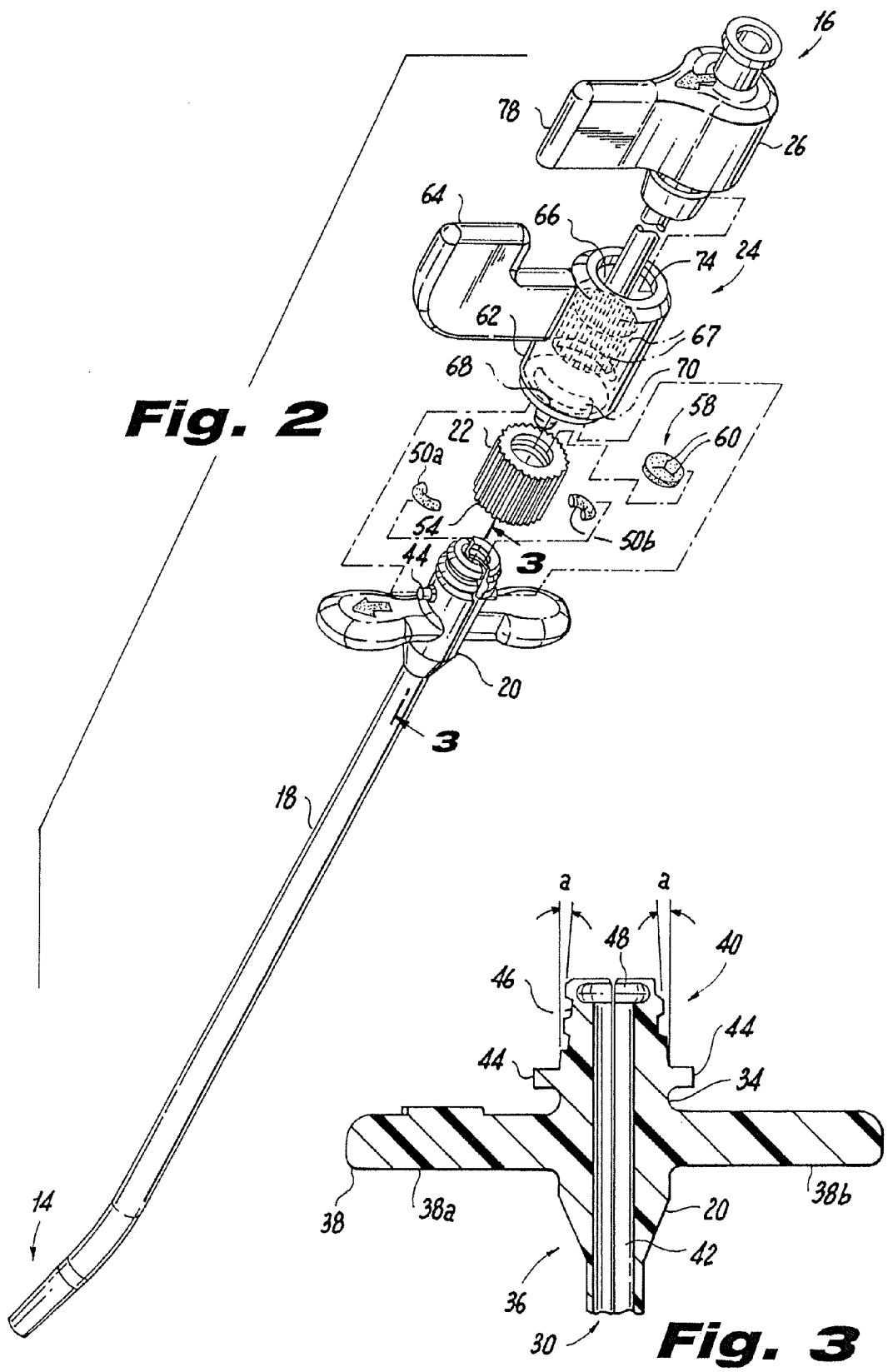

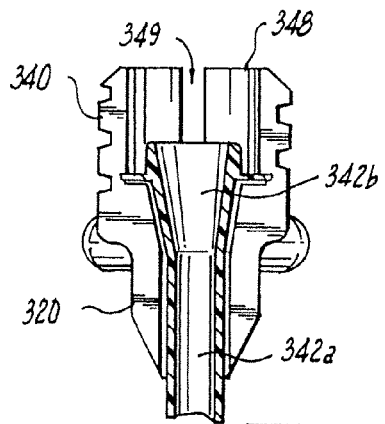
Fig. 29
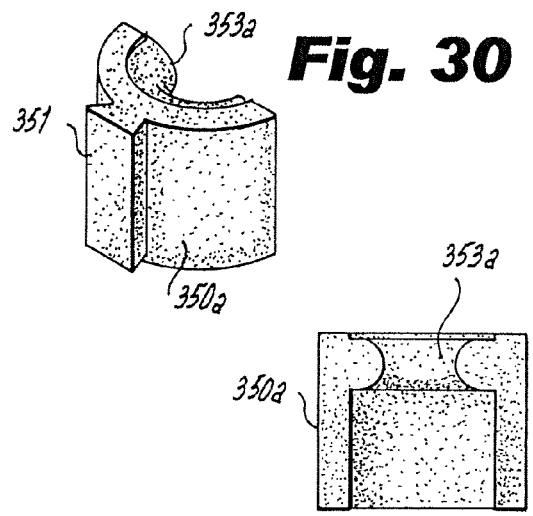
Fig. 30
Fig. 31
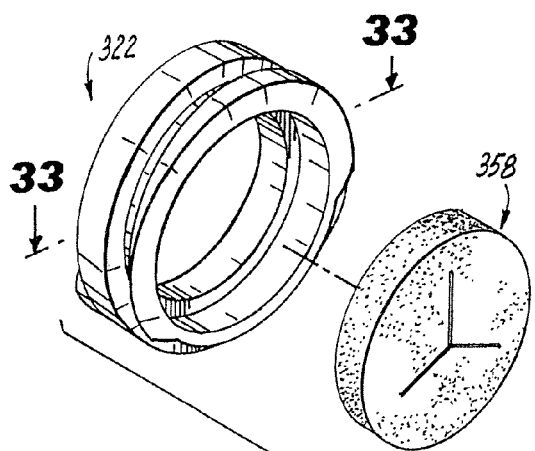
Fig. 32
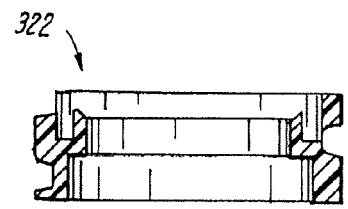
Fig. 33
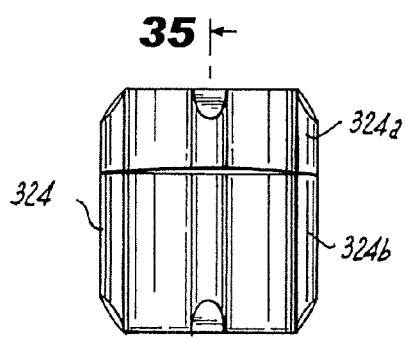
Fig. 34
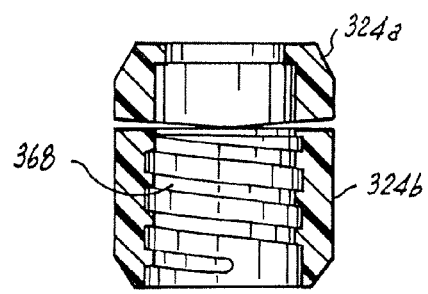
Fig. 35

VASCULAR INTRODUCER HAVING HEMOSTATIC VALVE WITH INTEGRAL SEAL

CROSS-REFERENCE TO RELATED APPLICATIONS

This application is a Continuation-in-Part application of U.S. patent application Ser. No. 10/940,415, filed Sep. 14, 2004, which is a Continuation-in-Part application of U.S. patent application Ser. No. 10/389,229 filed Mar. 14, 2003, now U.S. Pat. No. 7,192,433. This Application also claims priority to U.S. Provisional Patent Application Ser. No. 60/859,310 filed Nov. 16, 2006 and U.S. Provisional Patent Application Ser. No. 60/879,499 filed Jan. 9, 2007. Each of the foregoing applications is incorporated herein by reference in its entirety.

FIELD OF THE INVENTION

The present invention relates to vascular introducers. Particularly, the present invention is directed to seal assemblies for vascular introducers or other medical devices.

DESCRIPTION OF RELATED ART

The percutaneous introduction of diagnostic and/or therapeutic devices such as pacemaker leads and cardiovascular catheters into a blood vessel is typically accomplished with the aid of an introducer assembly. Introducer assemblies generally include a dilator having a tapered end portion and a thin-walled introducer sheath having a lumen extending therethrough to initially accommodate the dilator, and subsequently accommodate the passage of a pacemaker lead or catheter therethrough. Typically, the percutaneous introduction of an introducer assembly is accomplished by first inserting a needle into the blood vessel at a desired location and its position is verified by observing fluid return or by a similar method. While the needle is held firmly in place, a guidewire is inserted through the needle cannula to the desired depth. The guidewire is then held in place and the needle is withdrawn. Pressure is applied on the puncture site in order to minimize blood loss. Next, the introducer assembly is threaded over the guide wire. The introducer assembly is grasped close to the skin surface and advanced through the tissue to the desired position. Then, the dilator and guidewire are removed, leaving the sheath installed. A lead, catheter or similar diagnostic or therapeutic device is then introduced into the sheath and advanced to the desired position. Lastly, the sheath is removed, leaving the device disposed within the blood vessel of the patient.

It is known to configure an introducer sheath in such a manner so that it may be easily removed or separated from the lead or catheter after it has been emplaced. For example, it is known to provide score lines in the wall of the sheath to enable the sheath to be pealed away, slit or split open. Once the sheath is removed and catheter is emplaced, therapeutic medical devices such as endocardial pacing/defibrillation leads may be introduced into the blood vessel through the catheter.

Once the sheath is inserted into a blood vessel, it provides a passage for the free flow of blood. This may result in significant blood loss to the patient. The sheath also provides an open passage for the introduction of air into the vein. This could cause an embolism in the vascular system of the patient. To overcome these problems, vascular introducers have been developed with hemostatic valves that prevent the free flow of blood through the introducer sheath.

Examples of such devices are disclosed in U.S. Pat. No. 5,124,904 to Lee and U.S. Pat. No. 5,409,463 to Thomas et al., the disclosures of which are incorporated herein by reference in their entireties. In each of these devices, the hemostatic valve is configured in such a manner so that it creates frictional resistance to the passage of therapeutic devices such as flexible cardiac leads. This makes introduction of the lead difficult and can actually cause damage to the lead.

Other vascular introducers having hemostatic valves are known in the art, such as that disclosed in U.S. Pat. No. 6,966,896 to Kurth et al., the disclosure of which is incorporated herein by reference in its entirety. Examples of improved vascular introducers with selectively adjustable hemostatic valves are disclosed in U.S. Pat. No. 7,192,433 and U.S. Patent Application Publication No. 2005/0090779 to Osypka, which are also incorporated herein by reference in their entireties, as set forth above.

However, Applicant recognizes that these vascular introducers may still allow blood to exit through the introducer during the insertion process and emplacement of the medical device, and that there remains a need for a vascular introducer that inhibits such undesirable flow of blood. The present invention provides a solution for this and other problems.

SUMMARY OF THE INVENTION

The purpose and advantages of devices of the present invention are set forth in and apparent from the description that follows. Additional advantages of the invention will be realized and attained by the methods and systems particularly pointed out in the written description and claims hereof, as well as from the appended drawings.

To achieve these and other advantages, and in accordance with the purpose of the invention, among other things, a vascular introducer is provided having a proximal hub portion having an interior bore, an elongated sheath extending distally from the hub portion with a lumen in communication with the interior bore of the hub portion, and a hemostatic valve disposed within the bore of the hub portion. The hemostatic valve has a passage extending therethrough, and includes a sealing flap movable between an open position relative to the passage and a closed position relative to the passage.

The sealing flap can be arranged on a distal portion of the hemostatic valve and, if desired, can be integrally formed with the hemostatic valve. The sealing flap can be attached to the hemostatic valve with a hinge element integrally formed with the sealing flap. Moreover, the hinge can be formed with a predefined morphology to urge the sealing flap into the closed position. In alternate embodiments, the sealing flap is separately formed from the hemostatic valve and attached thereto.

Further, the sealing flap can have a convex proximal face configured to contact a distal end wall of the hemostatic valve when the sealing flap is in the closed position, and the distal end wall of the hemostatic valve can include a concave portion configured to complement the convex proximal face of the sealing flap to enhance a seal formed therebetween.

Vascular introducers in accordance with the invention can further include a second seal element provided within or near the bore of the hub portion, arranged proximally to the hemostatic valve also having a passage extending therethrough. The second seal element can have an annular aperture defined therein for sealingly engaging an outer circumference of a surgical implement inserted therethrough. If desired, the hemostatic valve and the second seal element can be integrally formed with one another or separately formed.

In accordance with another aspect of the invention, a vascular introducer is provided having a proximal hub portion having an interior bore, an elongated sheath extending distally from the hub portion and having a lumen in communication with the interior bore of the hub portion and a hemostatic valve disposed within the bore of the hub portion. The hemostatic valve can have a passage extending therethrough and can include a convexly contoured sealing flap movable between an open position relative to the passage and a closed position relative to the passage. The vascular introducer can further include a seal member located proximal to the hemostatic valve. Such seal member can be an annular seal member, which can be as simple as an O-ring type seal member or another suitable type of seal, such as a multi-cuspid valve. The seal member can be adapted and configured to seal against an instrument inserted therethrough, and can be a radially-expandable valve member configured to adjustably seal against different diameter instruments inserted therethrough.

The seal member can be integrally formed with the hemostatic valve and can further include a hinge element provided between the sealing flap and a body of the hemostatic valve. If desired, the sealing flap can instead be secured directly to a body of the hemostatic valve. Alternatively still, both the sealing flap and the body of the hemostatic valve can be attached to a separate intermediate element, which can be a housing, such as the hub of the vascular introducer, for example.

In accordance with a further embodiment of the invention, a method of inserting a vascularly introduced medical device is provided. The method includes the steps of providing a vascular introducer in accordance with the invention, as described hereinabove, inserting a needle into a blood vessel in a desired location, inserting a guidewire through the needle cannula to the desired depth, withdrawing the needle from the insertion site, leaving the guidewire protruding through the skin, threading the vascular introducer assembly over the guide wire, removing the dilator and guidewire, leaving the sheath of the introducer protruding through the skin into the blood vessel, introducing the medical device into the sheath, advancing the medical device to the desired position, and removing the sheath, leaving the medical device disposed within the blood vessel of the patient.

It is to be understood that both the foregoing general description and the following detailed description are exemplary and are intended to provide further explanation of the invention claimed.

BRIEF DESCRIPTION OF THE DRAWINGS

The accompanying drawings, which are incorporated in and constitute part of this specification, are included to illustrate and provide a further understanding of the devices and related methods and systems of the invention. Together with the description, the drawings serve to explain the principles of the invention, wherein:

FIG. 2 is an exploded perspective view of the vascular introducer assembly of FIG. 1 with parts separated for ease of illustration;

FIG. 3 is an enlarged cross sectional view of the hub portion of the vascular introducer assembly of FIG. 1;

FIG. 29 is an enlarged cross sectional view of the proximal end portion of the hub portion of the vascular introducer of FIG. 27, taken along the line 29-29 in FIG. 28, illustrating the threaded axial tab configuration, funnel entrance to the axial bore through the hub portion, and axial bores of differing diameter, among other things;

FIG. 30 is a perspective view of one part of the two-part sealing ring constructed in accordance with the present invention for use with the vascular introducer of FIG. 27, illustrating the arcuate shape, radially inward annular ring portion and outer notch for engaging the threaded axial tab on the proximal end portion of the hub portion of the vascular assembly shown in FIG. 27;

FIG. 31 is a front view of the part of the sealing ring shown in FIG. 30;

FIG. 32 is an exploded perspective view of the annular member constructed in accordance with the present invention for use with the vascular introducer of FIG. 27, illustrating the threaded exterior and trocar seal, among other things;

FIG. 33 is a cross sectional view of the annular member of FIG. 32, taken along line 33-33 in FIG. 32, illustrating the threading, among other things;

FIG. 34 is a front view of the locking collar constructed in accordance with the present invention, illustrating the location in which the locking collar can be separated into two parts;

FIG. 35 is a cross sectional view of the locking collar of FIG. 34, taken along line 35-35 in FIG. 34, illustrating the locking collar configuration including two separable portions, the first having an interior threading and the other being non-threaded, among other things;

These and other features of the vascular introducer assembly of the subject invention will become more readily apparent to those having ordinary skill in the art from the following description of the preferred embodiment.

DETAILED DESCRIPTION OF THE PREFERRED EMBODIMENT

In the following detailed description of the present invention, references are made to the accompanying drawings, in which are shown, by way of illustration, specific embodiments in which the invention may be practiced. These embodiments are described in sufficient detail to enable those skilled in the art to practice the invention, and it is to be understood that other embodiments may be utilized and that structural changes may be made without departing from the spirit and scope of the present invention. The following detailed description is, therefore not to be taken in a limiting sense, and the scope of the present invention is defined by the appended claims and equivalents thereof.

Figure 1:
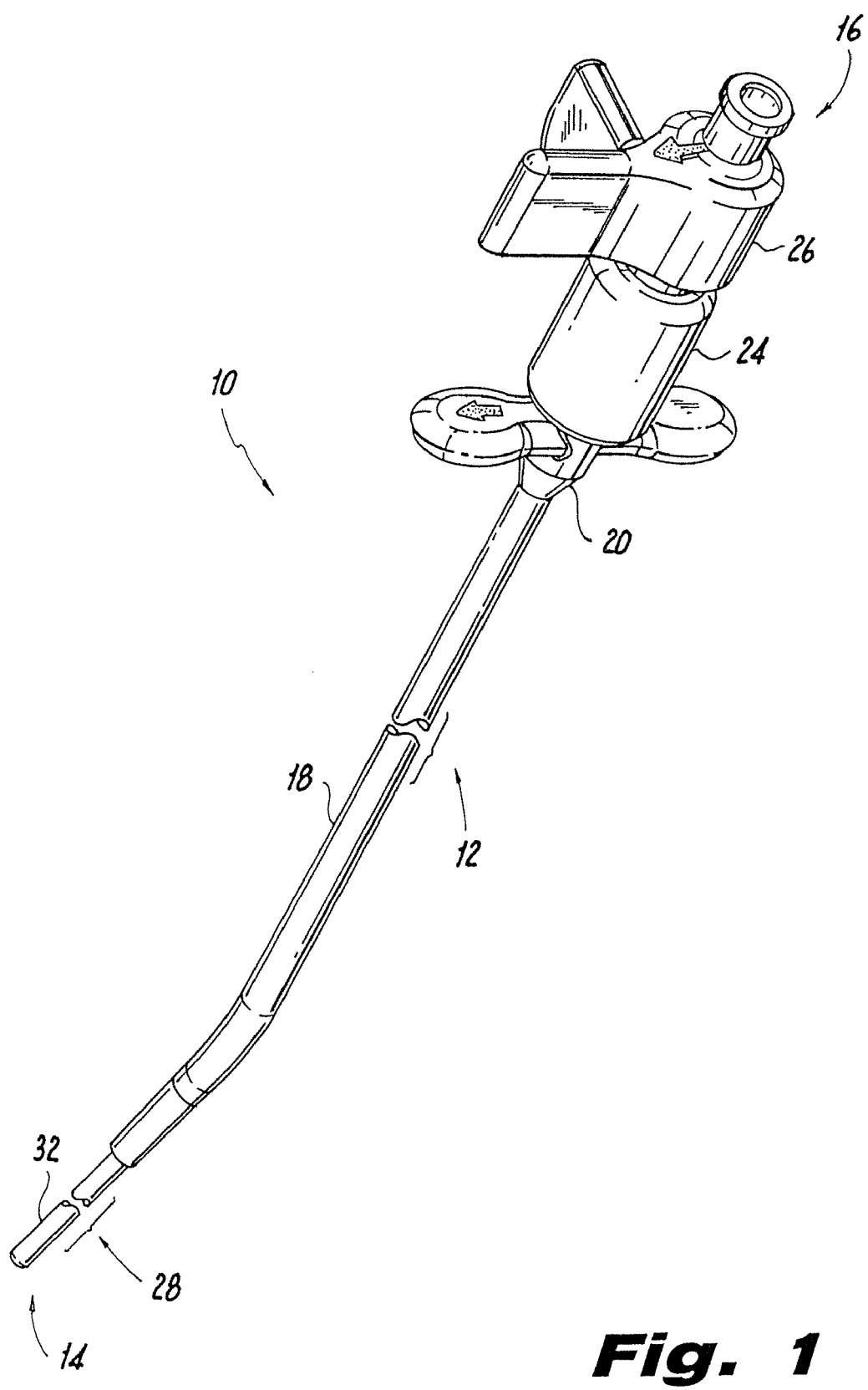
FIG. 1 is a perspective view of one embodiment of a vascular introducer assembly constructed in accordance with a preferred embodiment of the subject invention in a fully assembled condition.

Referring now to the drawings wherein like reference numerals identify similar structural features of the invention, there is illustrated in FIG. 1, a vascular introducer assembly constructed in accordance with a preferred embodiment of the subject invention and designated generally by reference numeral 10. Vascular introducer assembly 10 generally includes an elongated tubular body 12. The general shape and orientation of assembly 10 as shown in FIG. 1 defines a longitudinal axis and an axially opposed distal end 14 and proximal end 16 relative thereto, and these designations will be used as a convention throughout the following description to describe the components and features of the present invention.

Referring now to both FIGS. 1 and 2, this embodiment of introducer assembly 10 has a body 12 that generally includes (listed in order from distal end 14 to proximal end 16) an outer sheath 18, an engagement hub 20, a sealing cap 22, a locking collar 24 and a dilator handle 26, each of which are disposed over a hollow elongate dilator 28 and will be discussed in further detail herein below.

Figure 4:
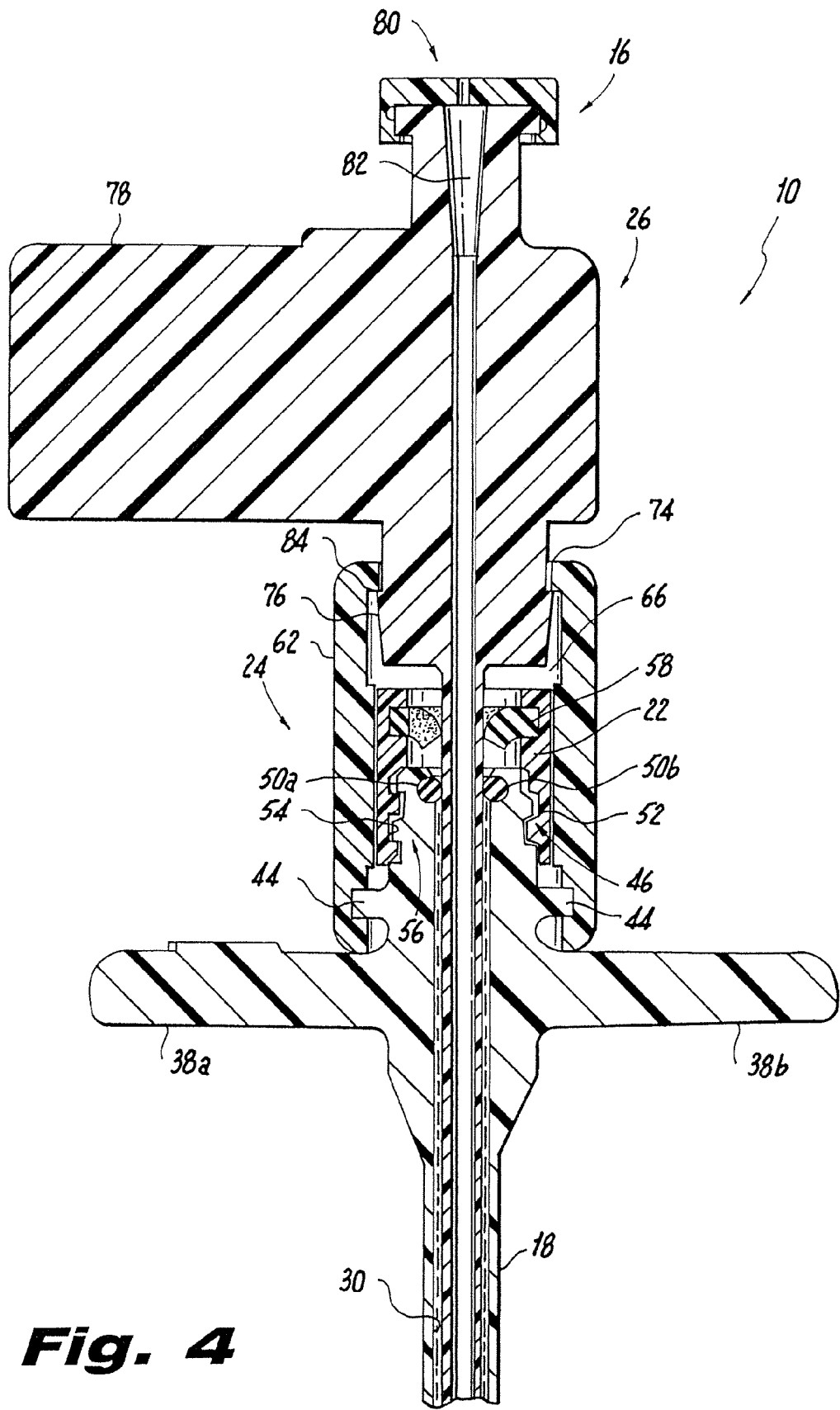
FIG. 4 is an enlarged cross sectional view of the proximal portion of the vascular introducer assembly of FIG. 1 with the rotatable locking collar in a locked position to prevent axial movement of the dilator relative to the sheath and the hemostatic seal in a closed position which restricts access through the axial lumen of the sheath.

Beginning with the distal-most component of assembly 10, outer sheath 18 is hollow and elongate. As shown in FIGS. 3 and 4, outer sheath 18 defines an interior axial lumen 30 for, among other things, accommodating dilator 28. As illustrated in this embodiment, dilator 28 includes a curved distal end portion 32, which, among other things, facilitates endocardial lead placement into areas of the heart that are difficult to access by intravascular means, such as the coronary sinus, but may also be straight or shaped in some other manner as well. Sheath 18 is preferably constructed of a compliant and flexible but resilient material that permits it to assume a curved form corresponding to the curvature of distal end portion 32. Preferably, sheath 18 is fabricated so that its shape may vary depending upon the intended use of the introducer.

Referring now to FIG. 3, along with continuing reference to FIGS. 1 and 2, engagement hub 20 generally includes a central body portion 34 having a tapered distal end portion 36, a sheath handle 38, a tapered proximal end portion 40 and an axial bore 42 therethrough in fluid communication with axial lumen 30. Tapered proximal end portion is sloped inwardly at an angle a, which is preferably between about 1 and about 8 degrees relative to the longitudinal axis defined by introducer 10. In this embodiment, sheath handle 38 includes a pair of opposing, radially outward projecting portions 38a and 38b. Preferably, the axial bore 42 is substantially aligned with and about the same diameter as axial lumen 30.

Proximal end portion 40 is fabricated of a flexible yet resilient material and includes a pair of opposed, radially outward projecting pins 44 positioned distally relative to a threaded portion 46 defined on the exterior of the proximal end portion 40, which is tapered as mentioned above so that its outer diameter generally decreases axially in the proximal direction. A circumferential channel 48 for receiving an annular sealing ring 50 therein is defined along the interior wall of proximal end portion 40 adjacent to its proximal end. Preferably, annular sealing ring 50 is fabricated from a flexible yet resilient material such as silicone. In this embodiment, annular sealing ring 50 includes a pair of semi-circular portions 50a and 50b.

Sealing cap 22 includes a body 52 having axially defined, substantially parallel grooves or flutes defined on its exterior and an axial bore 54 with a threaded portion 56 configured to engage the threaded portion 46 defined on the exterior of proximal end portion 40 of hub 20. Preferably, and as shown with specificity in FIG. 2, cap 22 further includes a trocar seal 58 disposed over axial bore 54 at the proximal end of cap 22.

Trocar seal 58 generally consists of a flexible but resilient material having three slits 60 defined therein which extend radially outward from its center to form three flaps. The three flaps may be forcibly opened to receive the dilator or other device while impeding fluid egress from the sealing cap 22.

Locking collar 24 includes a central body 62 having a single, radially outward projecting L-shaped handle 64 an axial bore 66 for receiving scaling cap 22. In this embodiment, axial bore 66 includes axially defined, substantially parallel grooves or flutes 67 for interlocking with the exterior scaling cap 22 so that rotational movement of collar 24 (i.e., movement not in the axial direction) results in the rotational movement of sealing cap 22 in accordance therewith. Collar 24 also includes a pair of slots 68 that are recessed in the interior wall of body 62 which defines axial bore 66 adjacent to the distal end of collar 24. Slots 68 are configured and dimensioned to receive pins 44 of hub 20 and cooperate together to secure locking collar 24 with the proximal end portion 40 of hub 20.

Slots 68 each include an axial portion 70 which extends in the proximal direction along the interior of collar 24 and is joined with a circumferential portion 72 that extends circumferentially along the interior periphery of collar 24. Collar 24 further includes a circular rim 74 defined at the proximal end of central body 56.

Dilator handle 26 includes a tapered distal stem portion 76, a single, radially outward projecting handle 78, a proximal receiving port 80 and an axial bore 82 therein. Tapered distal stem portion 76 includes a ridge 84 for engaging the circular rim 74 at the proximal end of collar 24 so that dilator handle 26 is rotatably mounted in the proximal end of collar 24. Axial bore 82 is in fluid communication with dilator 28 and proximal receiving port 80, thus, objects or devices such as endocardial leads may be inserted into dilator 28 via proximal receiving port 80.

Figure 5:
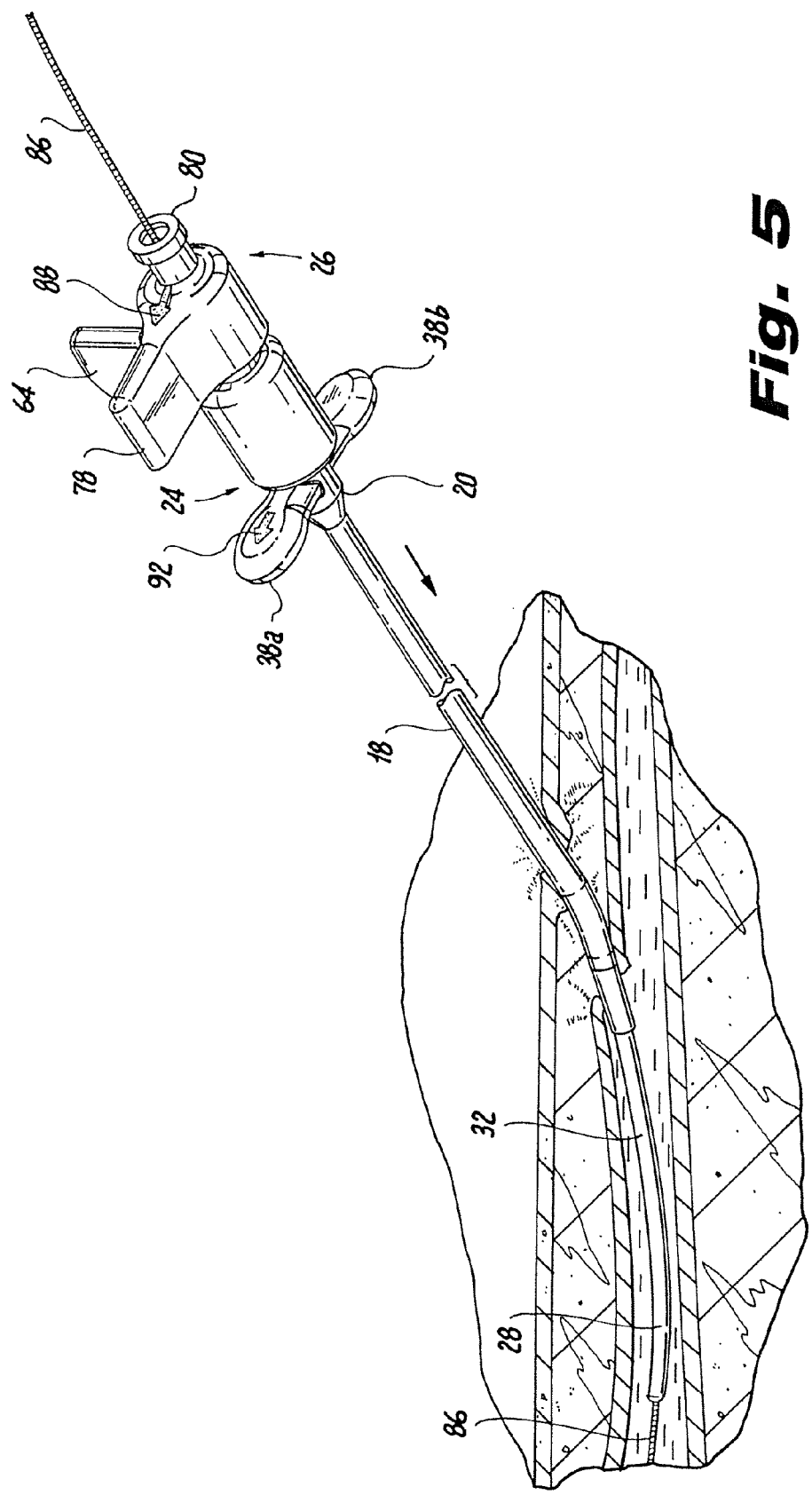
FIG. 5 is a perspective view of the vascular introducer assembly of FIG. 1 being percutaneously introduced into a blood vessel along a guidewire.

In use, the dilator 28 in vascular introducer assembly 10 is inserted over a guidewire 86, as shown in FIG. 5 and as described in the above background section. An arrow 88 is defined radially along the projecting handle 78 of dilator handle 26 to identify the relative direction of the curvature in distal end portion 32 of dilator 28. The locking collar 24, dilator handle 26 and sealing cap 22 cooperate to generally define a rotatable sheath lock and hemostatic seal. As Illustrated in FIG. 5, collar 24 is in the locked position on pins 44 (not shown in FIG. 5), which increases the rigidity and stability of the introducer assembly 10 for intravenous insertion, among other things.

As previously noted, rotational movement of collar 24 simultaneously causes the rotation of sealing cap 22, which is interlocked with collar 24 by flutes 67 in axial bore 66. As shown in FIG. 4, placing collar 24 in the locked position (i.e., pins 44 engaged within the circumferential portion 72 of slots 68) rotates sealing cap 22 in the clockwise direction on threaded portion 46 of the tapered proximal end portion 40 of huh 20. By twisting sealing cap 22 clockwise, cap 22 also moves distally with respect to proximal end portion 40, which causes a crimping action that forces proximal end portion 40 radially inward. This action reduces the diameter of axial bore 42 so that the annular sealing ring 50 at the proximal end of axial bore 42 closes around dilator 28, thus, impeding fluid (i.e., blood) flow entering via the distal end of lumen 30 from exiting through bore 42 and restricting insertion of devices into lumen 30.

Figure 6:
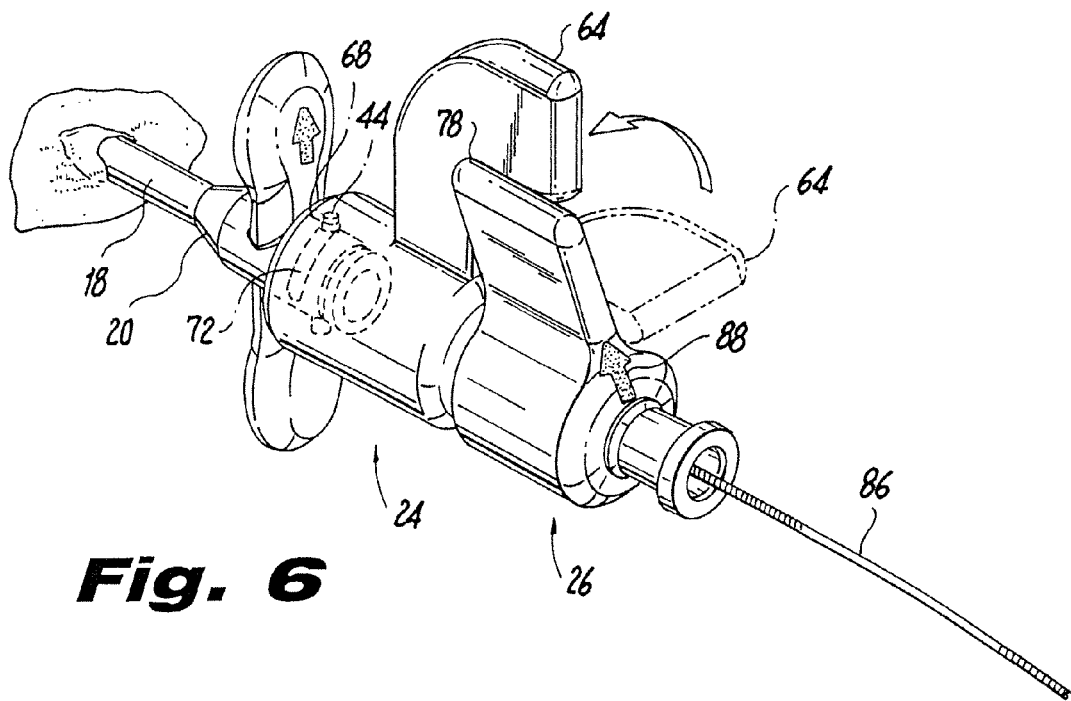
FIG. 6 is a perspective view of the proximal portion of the vascular introducer of FIG. 1 illustrating the rotational movement of the locking collar which moves the hemostatic seal to an open position in which passage of instruments through the axial lumen of the sheath is unrestricted.
Figure 7:
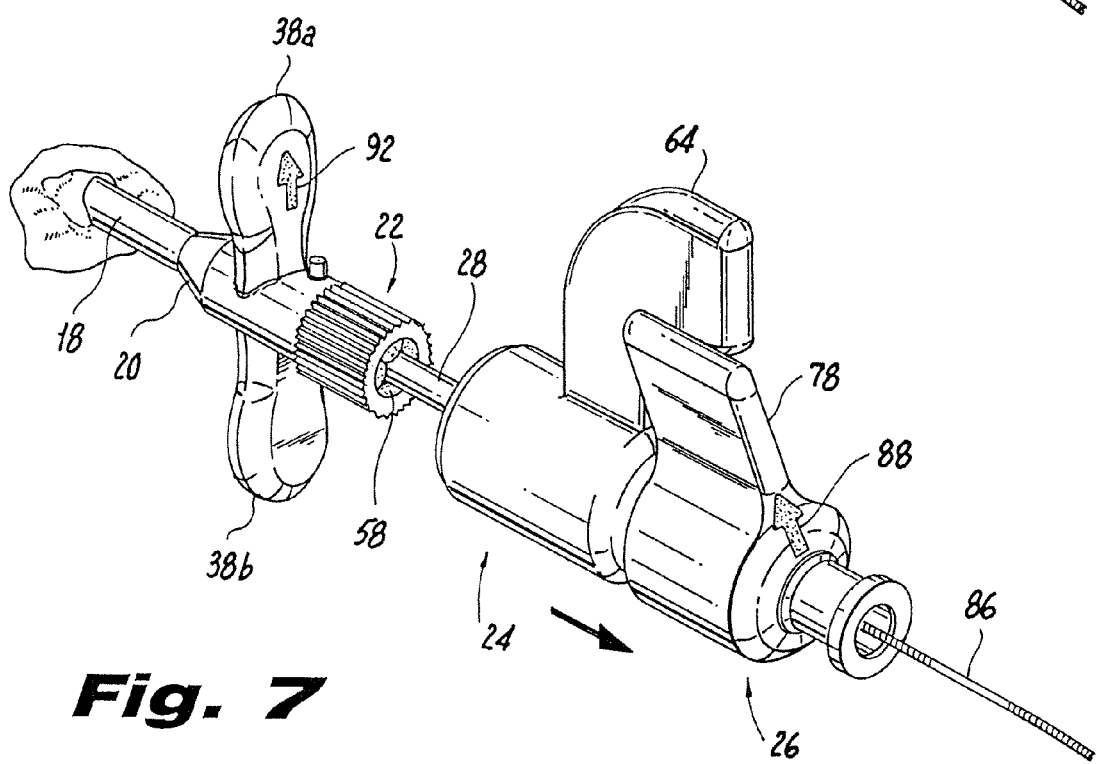
FIG. 7 is a perspective view of the vascular introducer of FIG. 1 illustrating the manner in which the rotatable locking collar and dilator are separated from the sheath and also showing the hemostatic seal which remains intact on the hub portion of the introducer.

Referring now to FIGS. 6 and 7, rotating collar 24 counterclockwise, so that outwardly projecting handle 64 of collar 26 is adjacent handle 78 on dilator handle 26, unlocks pins 44 from slots 68. Sealing cap 22 is also rotated counterclockwise which causes the movement of cap 22 along threaded portion 46 in the proximal direction which releases the aforementioned crimping action. Thus, fluid flow through axial bore 42 is no longer impeded by sealing ring 50. Preferably, the circumferential portions 72 of slots 68 in collar 24 are sufficiently elongated so that collar 24 can be fastened onto pins 44, or unfastened therefrom, by rotating the collar 24 about 90 degrees in either direction.

As shown in FIG. 7, rotating collar 24 to unlock collar 24 from pins 44 in hub allows the collar, along with dilator handle 26 and dilator 28, to move axially and be disengaged from the remaining components (i.e., sealing cap 22, hub 20 and outer sheath 18) in this embodiment of introducer assembly 10.

Figure 8:
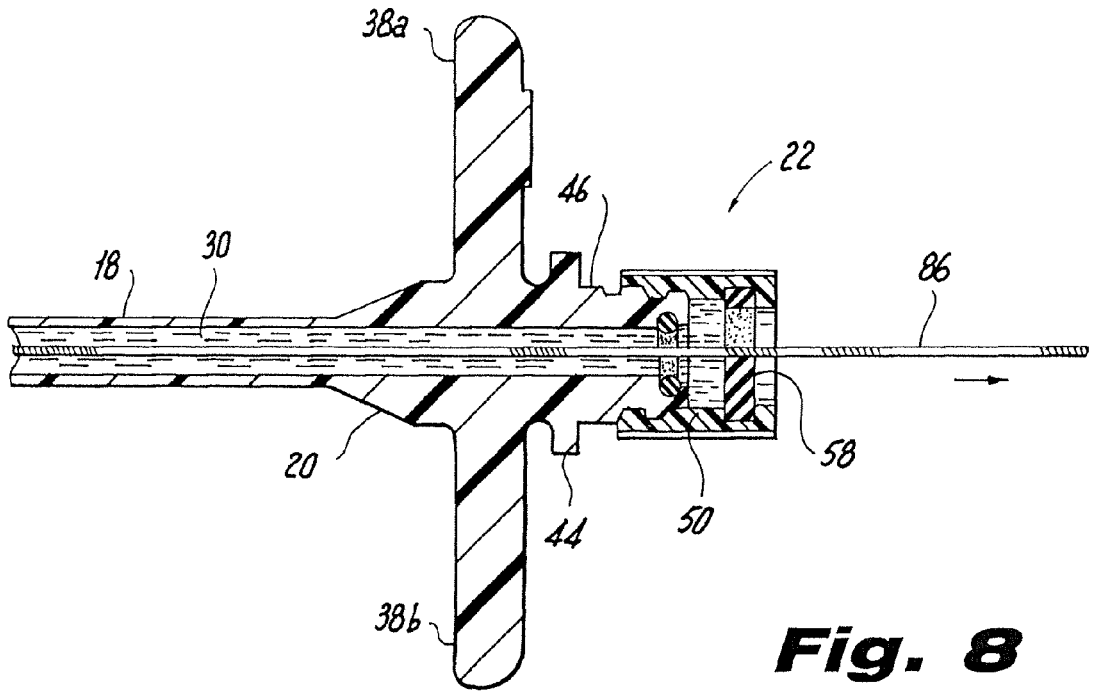
FIG. 8 is a cross sectional view of the hub portion and sealing cap of the vascular introducer assembly of FIG. 1 after the rotatable locking collar and dilator have been removed therefrom to illustrate the components of the present invention forming the adjustable hemostatic seal, with the seal being disposed in an open position in which passage of instruments through the axial lumen of the sheath is unrestricted.
Figure 9:
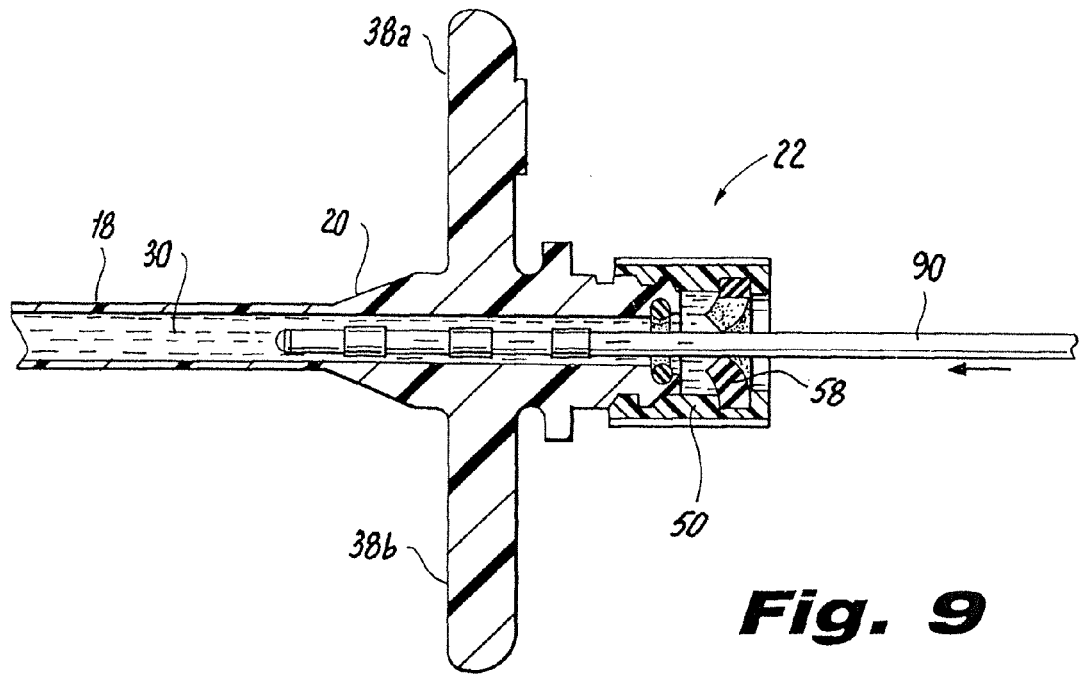
FIG. 9 is a cross sectional view of the hub portion and sealing cap as shown in FIG. 1, which illustrates the valve in an open position with an endocardial lead being inserted through the trocar seal of the sealing cap.
Figure 10:
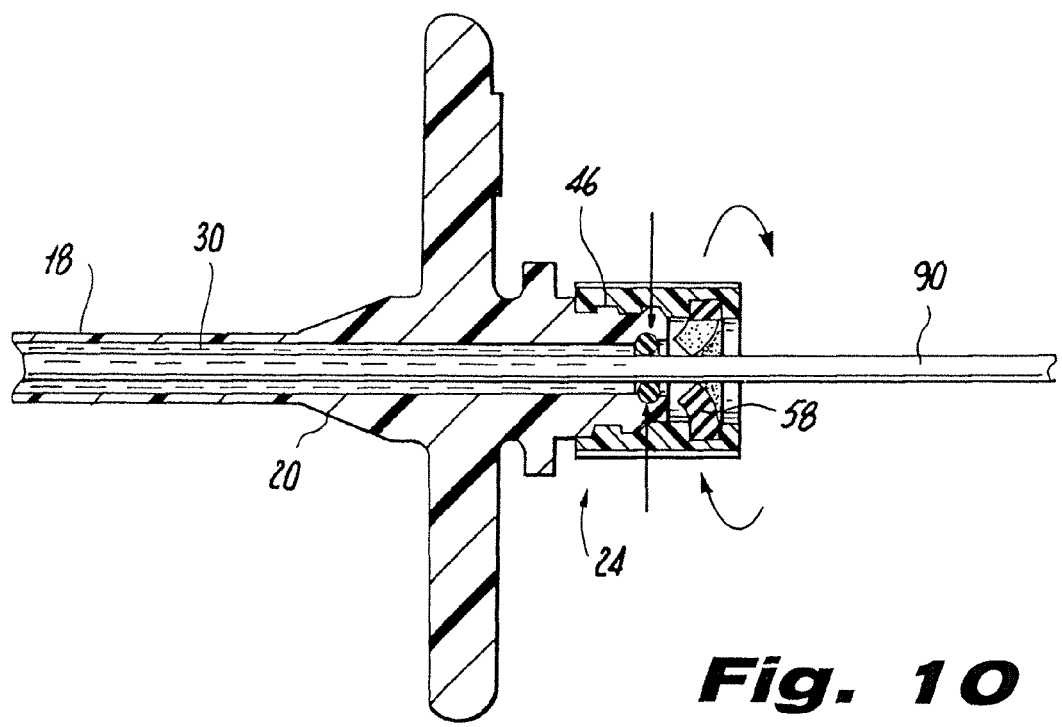
FIG. 10 is a cross sectional view of the hub portion and sealing cap shown in FIG. 9, along with the dilator disposed in the lumen of the introducer assembly, illustrating the movement of the sealing cap relative to the hub so that the hemostatic seal radially compresses around the dilator.

As shown in FIGS. 8 and 9, trocar seal 58 inhibits fluid flow entering lumen 30 from exiting cap 22 when collar 24, dilator handle 26 and dilator 28 are removed from introducer assembly 10. This allows guidewire 86 to be removed so that introducer assembly 10 may be used to insert devices or equipment, such as an endocardial lead 90, intravenously through lumen 30. In addition, dilator 28 and other associated components may be reinserted through lumen 30, and cap 22 may be threaded onto threaded portion 46 thereafter so that the aforementioned crimping action is applied, as shown in FIG. 10.

Figure 11:
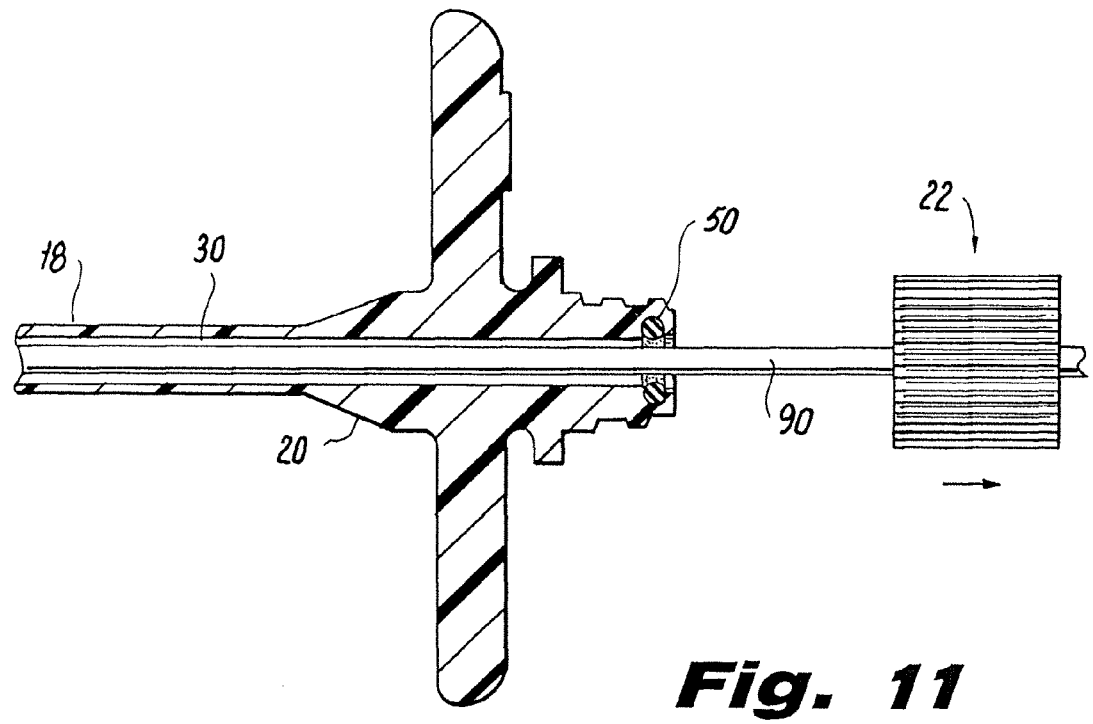
FIG. 11 is a cross sectional view of the hub portion of FIG. 10 illustrating the manner in which the sealing cap is removed from the hub when the hemostatic seal is in an open position.
Figure 12:
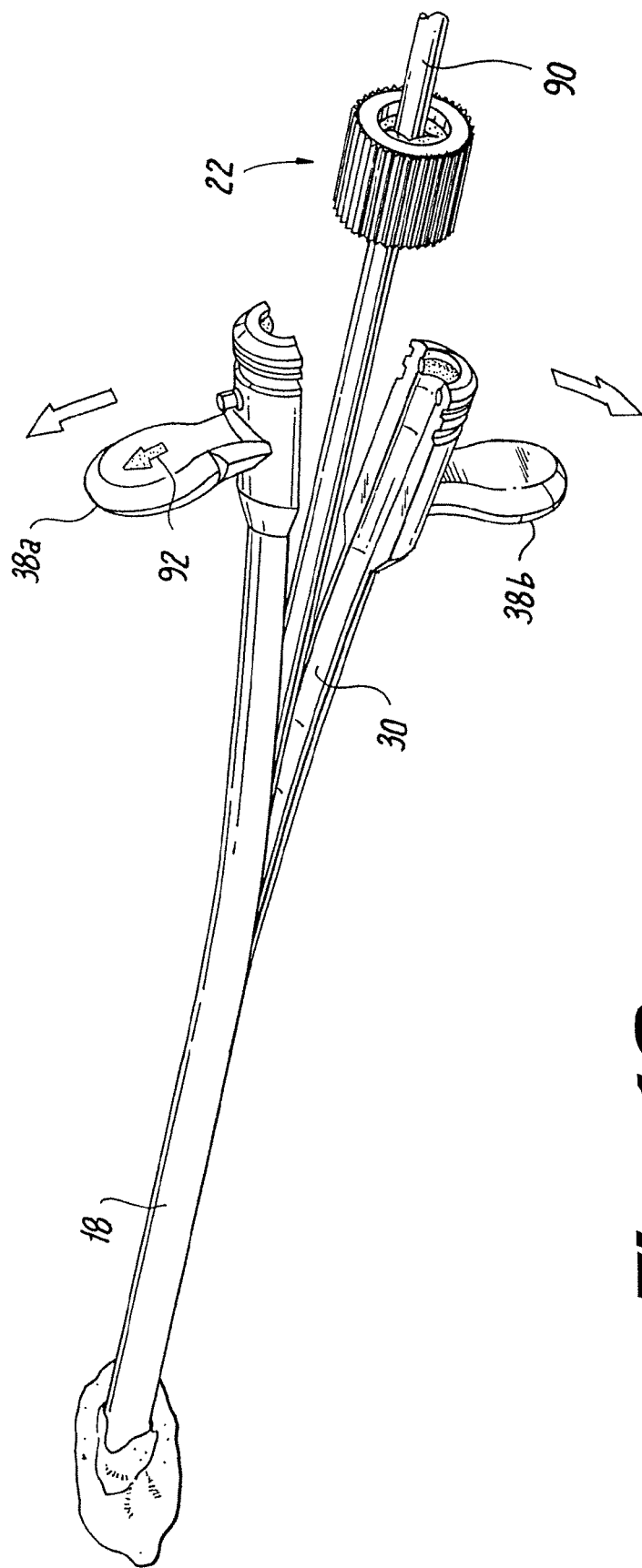
FIG. 12 is a perspective view of a vascular introducer assembly of the subject invention illustrating the manner in which the sheath is split along score lines to facilitate removal from the operative site.

As illustrated in FIG. 11, cap 22 may be threaded off and removed from hub 20. As described in the background section, this is essentially the first step in the removal of the introducer assembly 10, and facilitates removal of outer sheath 18 and hub 20. As shown in FIG. 12, in this embodiment, outer sheath 18 and hub 20 can be split substantially in half by pulling both handles 38a and 38b of hub 20 apart in opposing radial directions. Handle 38a is marked with an arrow 92 pointing in the radial direction as a guide. Preferably, outer sheath 18 and hub 20 are constructed with axially opposing weakened zones or score lines that facilitate dividing sheath 18 as shown in FIG. 12, without compromising the integrity of sheath 18 or restricting use of sheath 18 for any of its intended purposes.

FIGS. 13-24 disclose another embodiment of a vascular introducer assembly constructed in accordance with the present invention which is designated generally by the reference numeral 110. Body 112 of introducer assembly 110 includes (from distal end 114 to proximal end 116) an outer sheath 118, an engagement hub 120, a fluted sealing cap 122, a locking collar 124 and a dilator handle 126, which are all configured and dimensioned for being disposed over a dilator 128.

In this embodiment, the proximal end portion 140 of hub 120 includes a proximal threaded portion 146 which corresponds with and is configured to engage threaded portion 156 defined within sealing cap 122. A distal threaded portion 144 is also defined on the proximal end portion 140 of hub 120 that is configured to engage threads 168 defined on the distal portion of the interior of locking collar 124 for securing locking collar 124 to hub 120. As in previous embodiments, locking collar 124 is connected at the proximal end with dilator handle 126 in a manner which permits rotational movement of dilator 128.

Also in this embodiment, axial bore 142 of hub 120 includes a distal end portion 142a having a first diameter, which extends through the majority of hub 120, and a proximal end portion 142b having a second diameter, which extends primarily through proximal end portion 140. The second diameter of proximal end portion 142b is configured and dimensioned to be of sufficient size to receive devices for intravenous insertion without jeopardizing the effectiveness of seal 150 in forming a fluid tight seal with dilator 128 when actuated to do so by sealing cap 122. In this embodiment, the second diameter in bore 142b is larger than the first diameter of bore 142a.

Proximal end portion 140 also includes four independent axial tabs 148 that define four axial slots 149. Axial tabs 148 each include a partial threading thereon which taken together form threaded portion 146 for receiving sealing cap 122. As can be best viewed in FIG. 15, two of the four axial slots 149 are keyed or otherwise shaped for receiving a triangular notch 151 on cylindrical sealing tube 150 with a radially inward projecting ring 153. Sealing tube 150 is divided into two symmetrical semi-cylindrical or "half-pipe" sections 150a and 150b, each including a substantially half portion of radially inward projecting ring 153, referred to as half-rings 153a and 153b, respectively.

Figure 13:
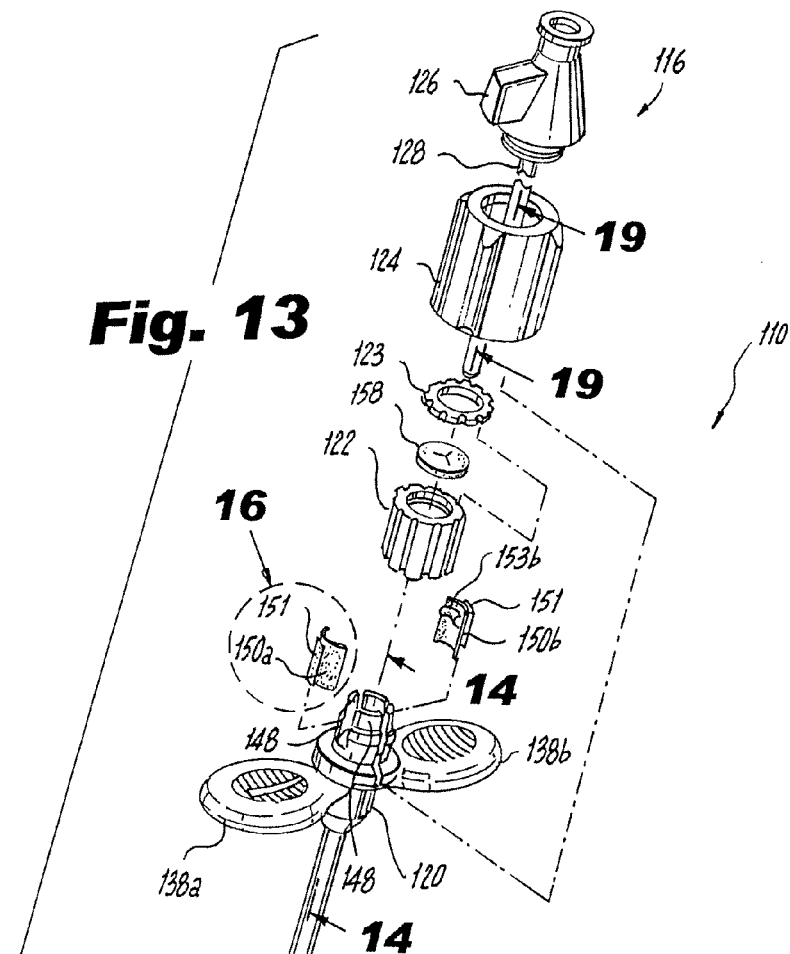
FIG. 13 is an exploded perspective view of a vascular introducer assembly constructed in accordance with another preferred embodiment of the subject invention with parts separated for ease of illustration.
Figure 14:
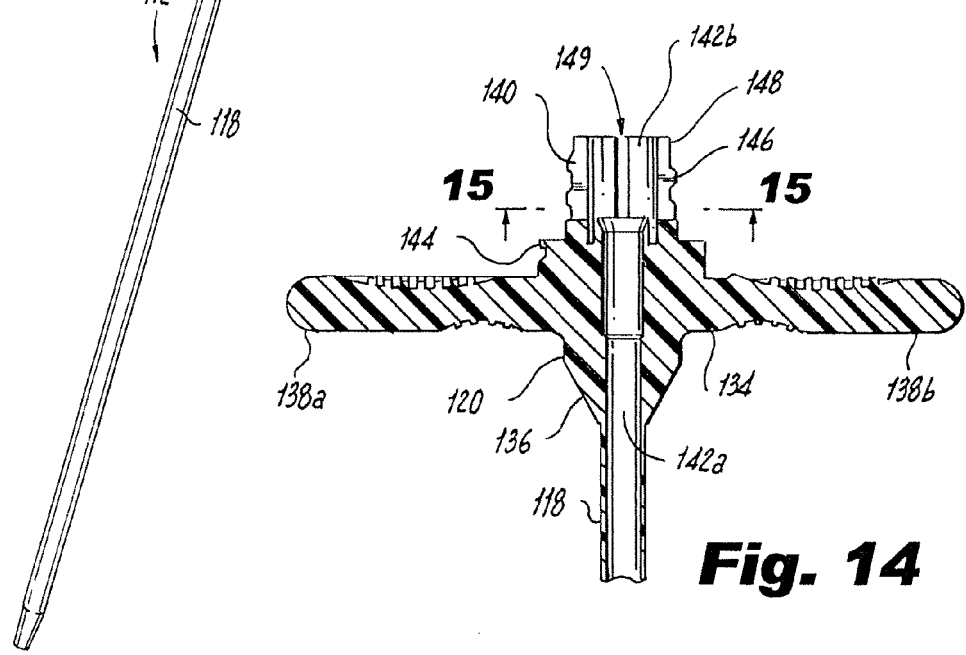
FIG. 14 is an enlarged cross sectional view of the hub portion of the vascular introducer assembly of FIG. 13.
Figure 15:
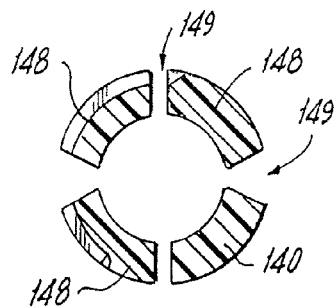
FIG. 15 is an enlarged cross sectional view of the proximal end portion of the hub portion of the vascular introducer of FIG. 13, taken along the line 15-15 in FIG. 14, illustrating the threaded axial tab configuration.
Figure 16:
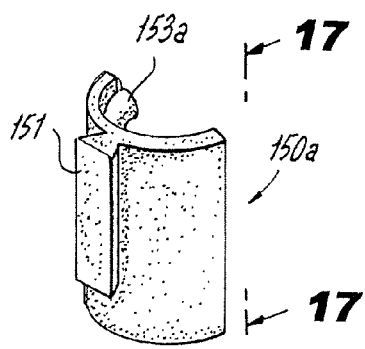
FIG. 16 is a perspective view of one part of the two-part sealing ring constructed in accordance with the present invention for use with the vascular introducer of FIG. 13, illustrating the arcuate shape, radially inward annular ring portion and outer notch for engaging the threaded axial tab on the proximal end portion of the hub portion of the vascular assembly shown in FIG. 13.
Figure 17:
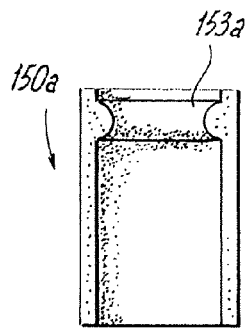
FIG. 17 is a front view of the part of the sealing ring shown in FIG. 16, taken along line 17-17 in FIG. 16.
Figure 19:
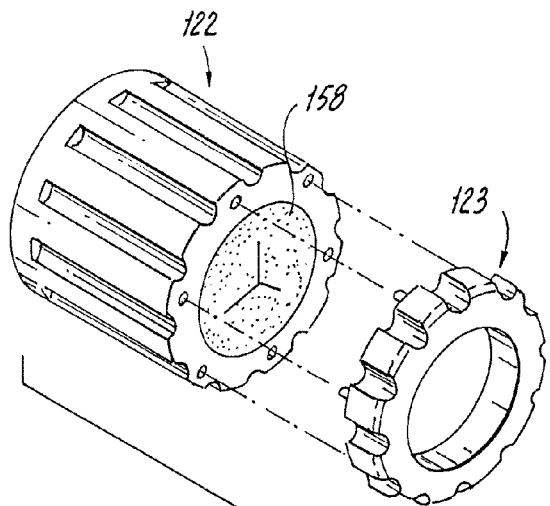
FIG. 19 is a cross sectional view of the locking collar constructed in accordance with the present invention for use with the vascular introducer of FIG. 13, taken along line 19-19 in FIG. 13, illustrating the threaded portion therein, among other things.

As can be best viewed in FIGS. 13 and 17, half-rings 153a and 153b are adjacent the proximal end of each half-pipe sections 150a and 150b and together generally form a circle of smaller diameter than the diameter of the circle formed by half-pipe sections 150a and 150b. The other two slots 149 in proximal end portion 140 that do not receive a triangular notch 151 facilitate a tight seal of the passageway by being sufficiently pliable to be moved radially inward to restrict axial bore 142b when a crimping action is applied to proximal end portion 140 by the distal threading of sealing cap 122.

Figure 18:
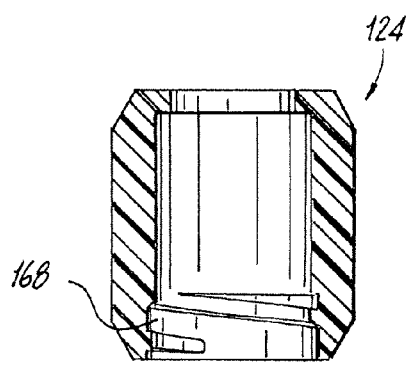
FIG. 18 is an exploded perspective view of the sealing cap member constructed in accordance with the present invention for use with the vascular introducer of FIG. 13, illustrating the trocar seal and removable proximal ring portion, among other things.

As shown best in FIG. 18, sealing cap 122 of this embodiment includes a removable annular rim 123 at its proximal end. Annular rim 123 is secured to cap 122 by dowels 125 which preferably snap-fit into holes 127. A trocar seal 158 is disposed over axial bore 154 through sealing cap 122, and is secured in part by the engagement of annular rim 123 with cap 122. Threads 168 are defined on the distal portion of the interior surface of cap 122.

Figure 20:
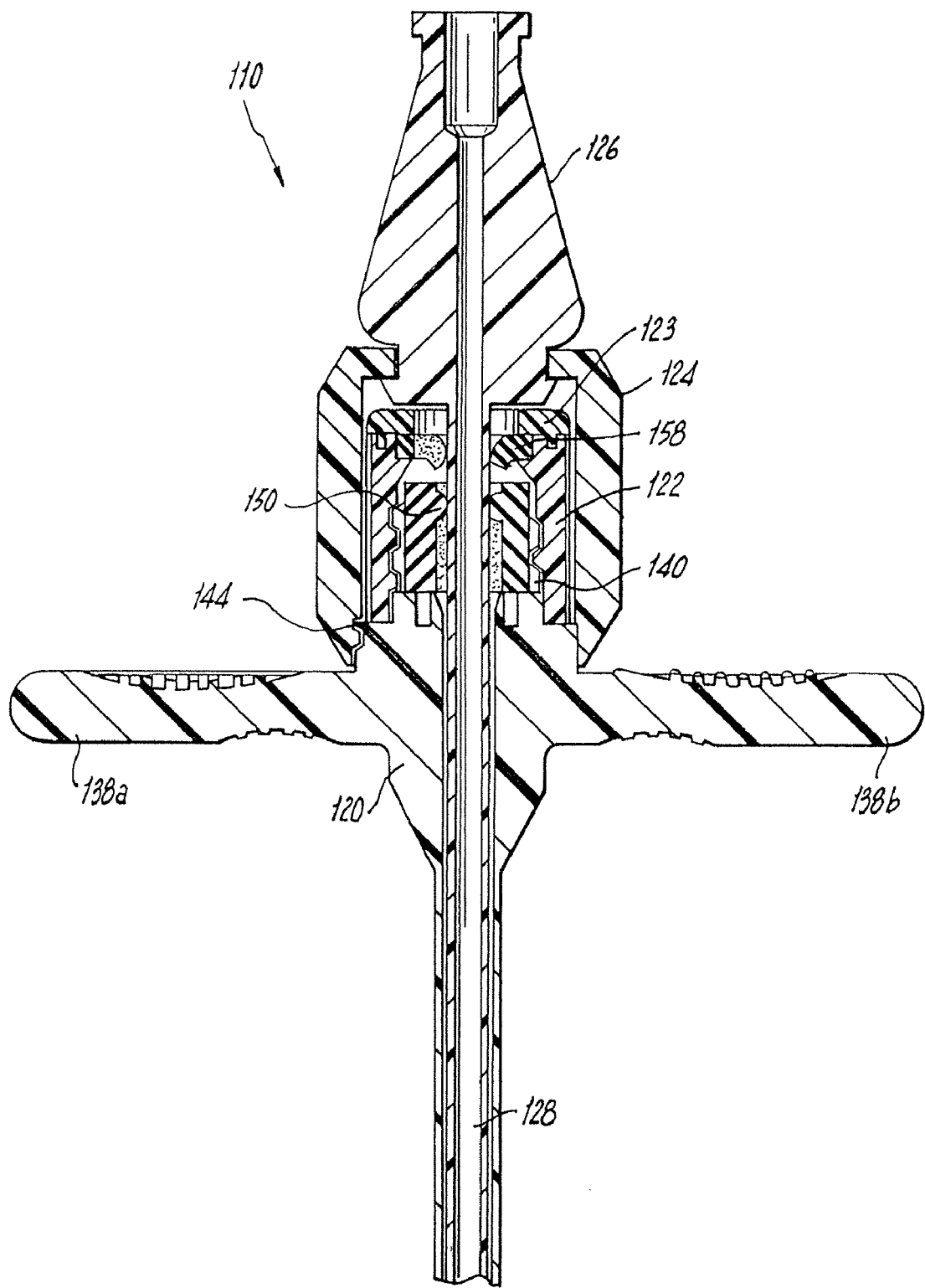
FIG. 20 is a cross sectional view of the vascular introducer of FIG. 13, illustrating the locking collar, sealing cap, dilator handle and dilator secured on the hub portion in a configuration which prevents blood flow through the hemostatic valve and impedes axial movement of the dilator relative to the hub portion through compression of the hemostatic valve against the dilator within the hub portion of the assembly.

FIG. 20 illustrates vascular assembly 110 wherein sealing cap 122 is fully (i.e., as far in the distal direction as possible) threaded onto threads 146 on proximal end portion 140 of hub 120, and locking collar 124 is disposed over cap 122 and fully threaded onto threads 144 on proximal end portion 140 of hub 120. Dilator 128 extends through introducer 110 contacting trocar seal 158 in sealing cap 122, and as explained below, contacting half-rings 153a and 153b of sealing ring 150.

In this configuration, locking collar 124 is fully threaded onto hub 120 preferably by twisting clockwise, which moves both locking collar 124 and sealing cap 122 distally relative to proximal end portion 140. Thus, sealing cap 122 bears down on axial tabs 148 causing a chain reaction of radially inward motion starting with axial tabs 148 and then progressing to both sealing tube halves 150a and 150b. The radial inward position of sealing tube halves 150a and 150b results in contact between half-rings 153a and 153b on tube halves 150a and 150b and dilator 128 which impedes axial movement of dilator 128 and restricts blood flow from exiting hub 120 in the proximal direction.

Figure 21:
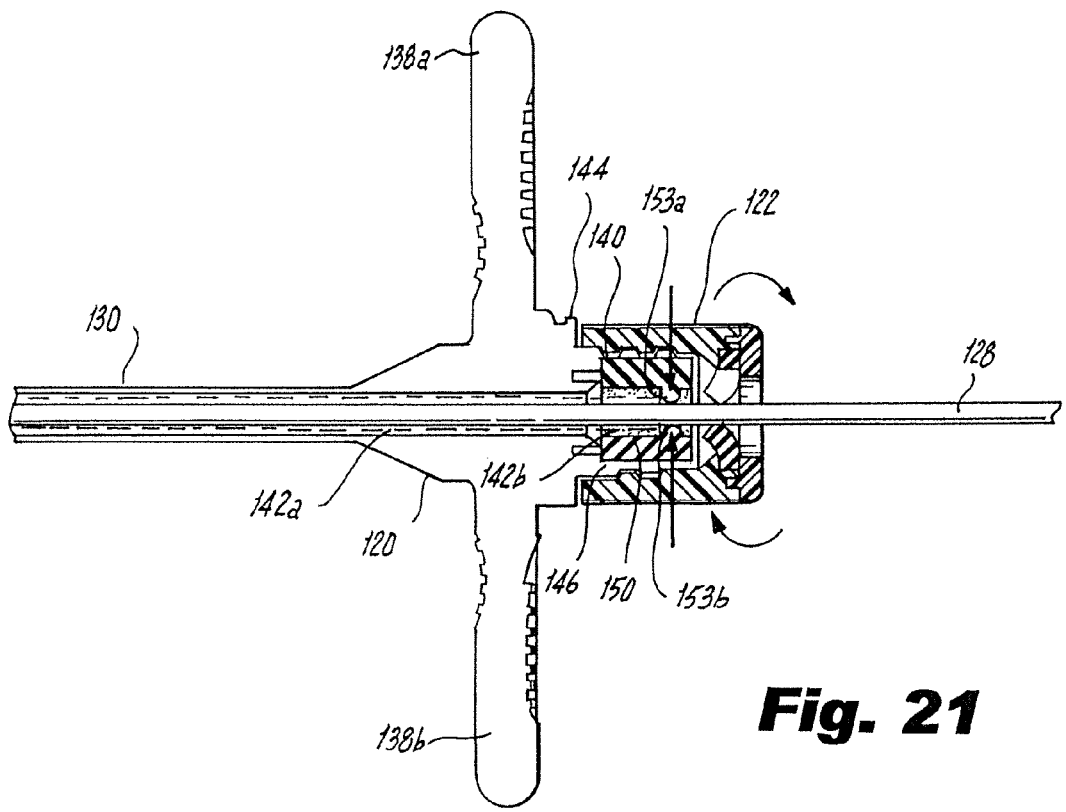
FIG. 21 is cross sectional close up view of the hub portion of the vascular introducer of FIG. 13, illustrating the manner in which the locking collar, dilator handle and dilator are separated from the hub portion and hemostatic valve formed by the sealing cap member, among other things.

FIG. 21 illustrates the introducer assembly 110 during the process of removing locking collar 124 (not shown) and dilator handle 126 (not shown) along with dilator 128 in the proximal direction away from hub 120. Locking cap 124 can be de-threaded from hub 120 and separated from vascular assembly 110 while sealing cap 122 remains in place. Sealing cap 122 is shown as being completely threaded upon the threaded portion 146 of proximal end portion 140. Thus, pressure is applied to cause a crimping action on proximal end portion resulting in the radially inward movement of sealing tube 150.

In this state, dilator 128 may be moved from axially and separated from introducer assembly 110, although it is somewhat impeded by contact with half-rings 153a and 153b. However, the contact with half-rings 153a and 153b substantially restricts blood flow through hub 120 while dilator 128 is being removed. When dilator 128 is fully separated from introducer 110, blood may flow further proximally than sealing tube 150 but is substantially restricted by trocar seal 158.

Figure 22:
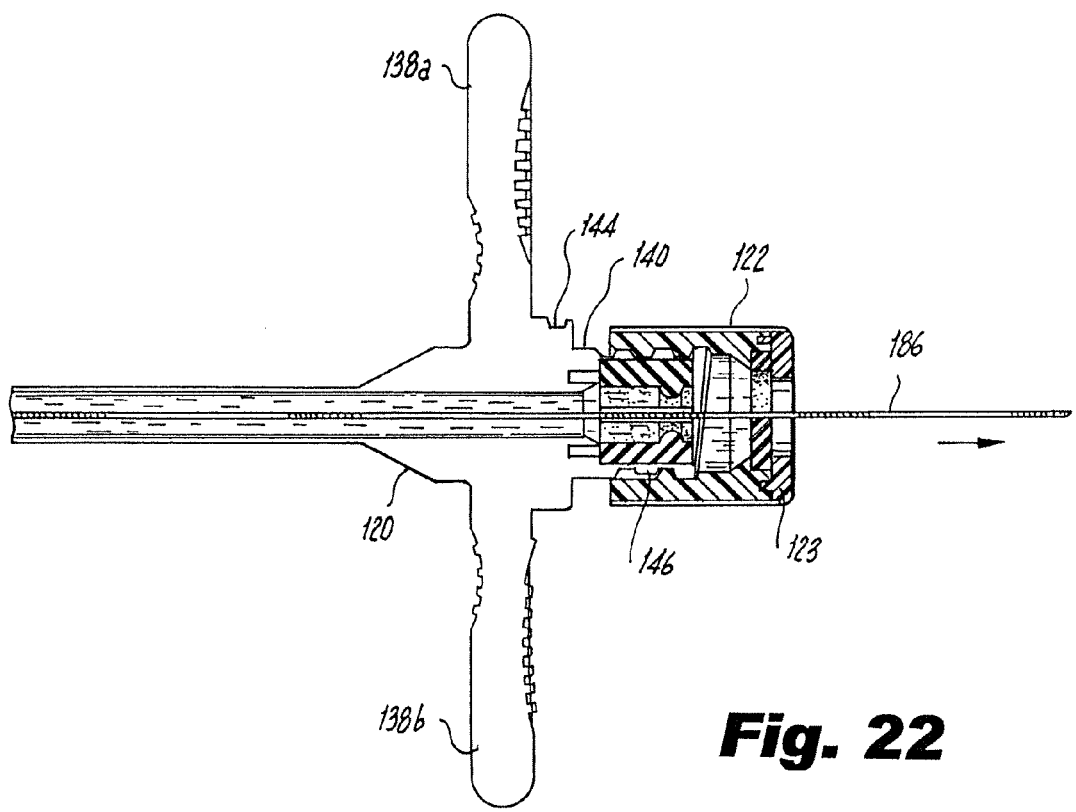
FIG. 22 is cross sectional close up view of the hub portion of the vascular introducer of FIG. 13 without the locking collar, dilator handle and dilator, illustrating the manner in which a guidewire extends through the hub portion and hemostatic valve.

As shown in FIG. 22, dilator 128 has been removed, revealing guidewire 186 which extends through introducer assembly 110 in its place. Cap 122 has been de-threaded along threaded portion 146 on proximal end portion 140, which releases the crimping action and pressure placed on proximal end portion 140, allowing sealing tube 150 to move radially outward to a rest position. In this position, blood can flow freely through axial bore 142b and 142a of hub 120 without being impeded by annular half-rings 153a and 153b. Trocar seal 158 on cap 122 restricts any blood flow from exiting introducer 110.

Figure 23:
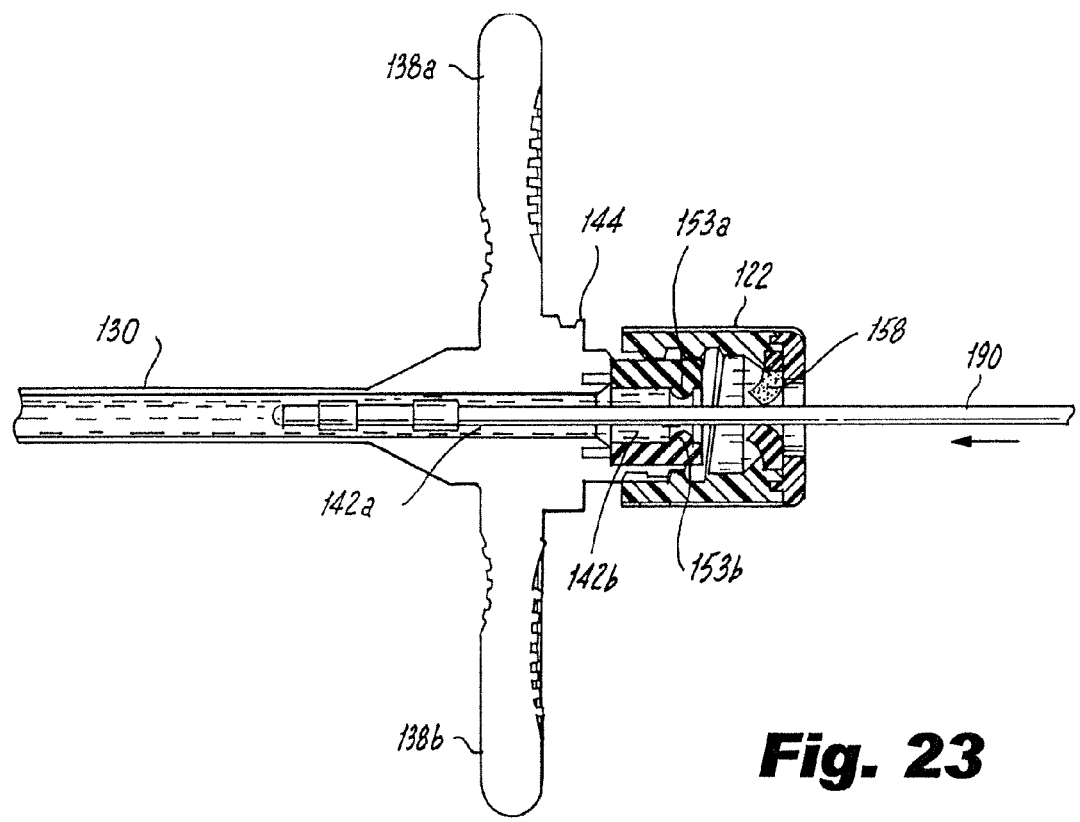
FIG. 23 is cross sectional close up view of the hub portion of the vascular introducer of FIG. 13, without the locking collar, dilator handle and dilator, illustrating the sealing cap member in a configuration which releases the radially inward pressure on the sealing members for facilitating insertion of an endocardial lead through the hub portion.
Figure 24:
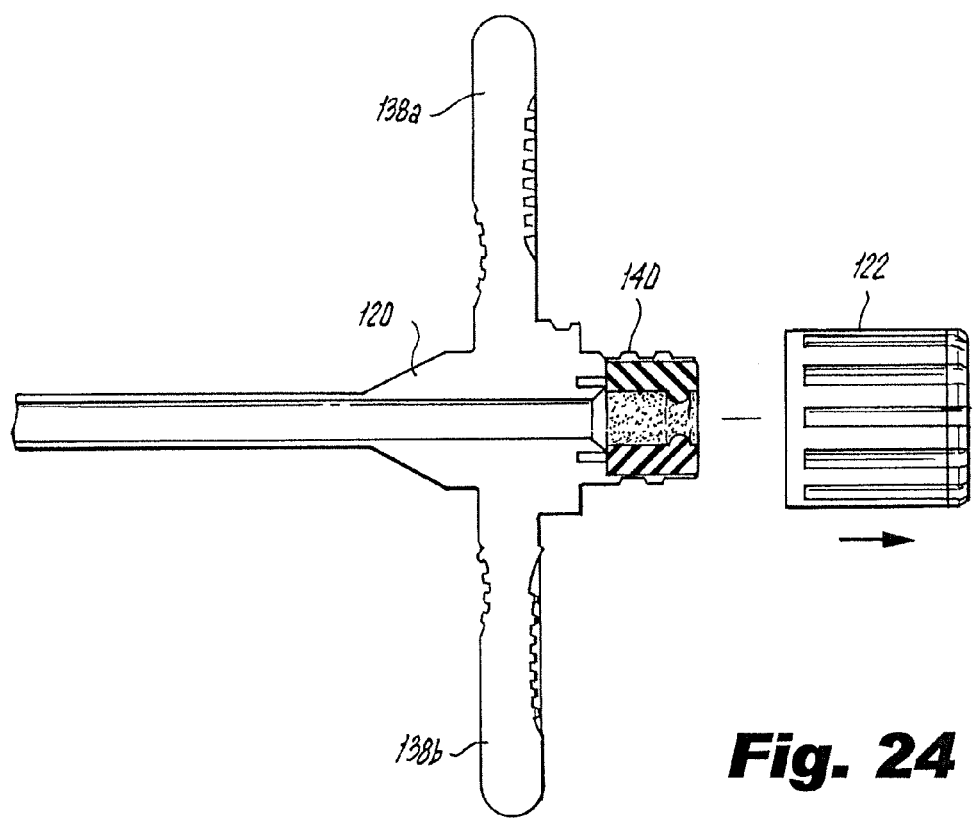
FIG. 24 is cross sectional close up view of the hub portion of the vascular introducer of FIG. 13, without the locking collar, dilator handle and dilator, illustrating the separation of the sealing cap member from the hub portion.

Once guide wire 186 has been separated from introducer 110, introducer 110 can be used to insert devices or equipment intravenously through the axial bores in sealing cap 122, hub 120 and lumen 130, such as endocardial lead 190 as shown in FIG. 23. Sealing cap 122 can be fully de-threaded and removed from proximal end portion 140 to permit blood to flow through introducer 110 without restriction. In addition, once sealing cap 122 is removed, the remaining introducer 110 can be split by pulling apart handles 138a and 138b in the manner described with regard to introducer assembly 10 of the previous embodiment.

Figure 25:
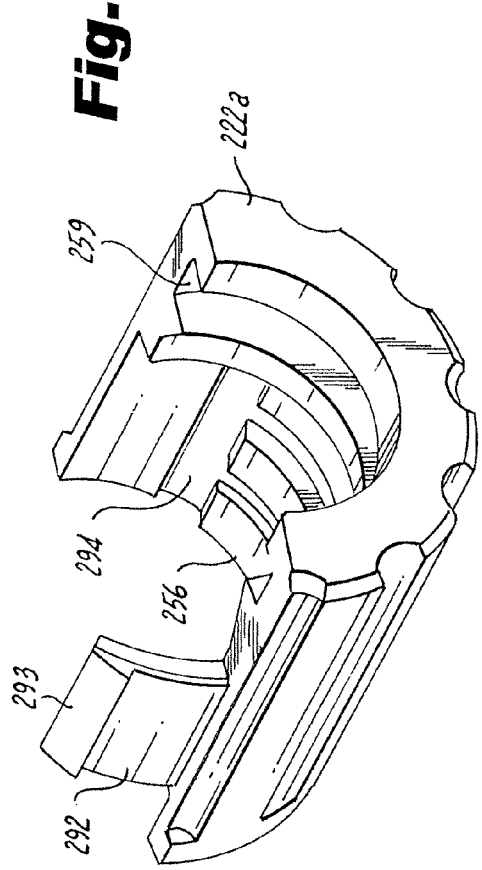
FIG. 25 is a perspective view of one part of a two-part splittable sealing cap member constructed in accordance with another preferred embodiment of the present invention, illustrating the interlocking features, among other things.
Figure 26:
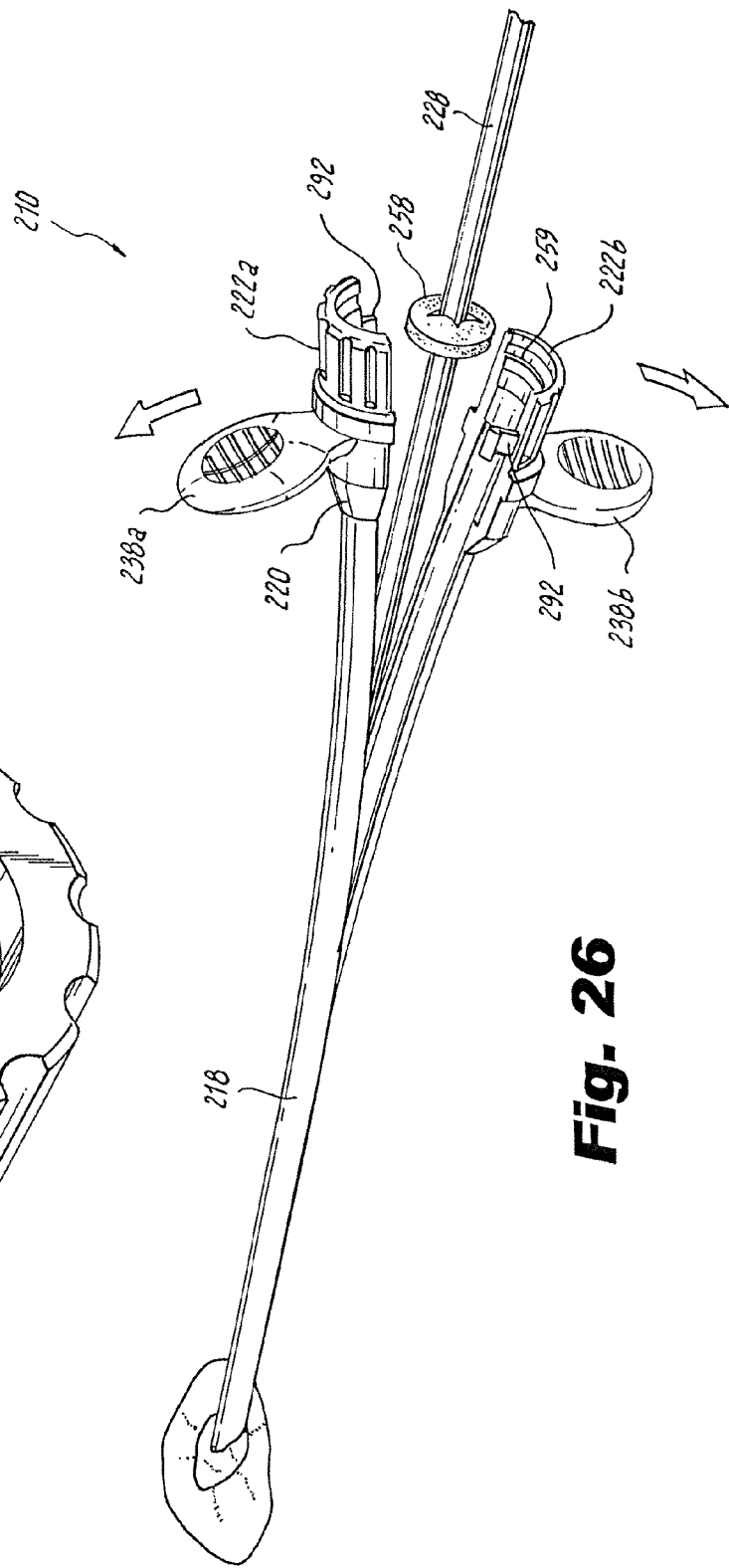
FIG. 26 is a perspective view of a vascular introducer featuring the splittable sealing cap member of FIG. 25, illustrating the manner in which the introducer and sealing cap member can be slit together leaving the trocar seal on the dilator.

In another embodiment, a vascular introducer constructed in accordance with the present invention can include a splittable sealing cap 222 as illustrated in FIGS. 25-26. Vascular introducer 210 includes a sealing cap 222, which can be split longitudinally to form corresponding symmetrical halves 222a and 222b.

Each half sealing cap 222a and 222b includes a circumferentially projecting tab 292 with a ramped end portion 293 thereon. A receiving portion 294 is defined on each half sealing cap 222a and 222b for engaging the projecting tab 292 and ramped end portion 293 of the other sealing cap halves 222a or 222b when cap 222 is assembled. A threaded portion 256 is formed in the interior surface of sealing cap 222 by assembling half caps 222a and 222b. Threads 256 are configured to be engage a threaded portion 246 (not shown) on proximal end portion 240 (not shown). A trocar seal 258 is secured within a groove 259 defined on the interior surfaces of both sealing cap halves 222a and 222b proximally adjacent threaded portion 256.

Sealing cap 222 functions similarly to the previous embodiments to actuate the sealing feature associated with introducer 210 of the present invention. By threading sealing cap 222 onto proximal end portion 240, seal 250 contacts dilator 228 to prevent blood flow proximally through introducer 210. By de-threading sealing cap 222, the flow of blood is permitted through proximal end portion 240 but is stopped by trocar seal 258 of sealing cap 222.

Introducer 210 can be split while sealing cap 222 is in place, provided locking collar 224 (not shown) along with dilator handle 226 (not shown) are removed from introducer 210 prior thereto. As shown in FIG. 26, with sealing cap 222 securely threaded on hub 220 of introducer 210, ramped ends 293 of the sealing cap halves 222a and 222b can be disengaged from their respective receiving portions 294 by pulling handles 238a and 238b in opposing directions. Sealing cap 222 divides into halves 222a and 222b and is thus split along with hub 220 and lumen 218.

FIGS. 27-40 illustrate another embodiment of a vascular introducer assembly constructed in accordance with the present invention and generally designated by the reference numeral 310. This embodiment includes a threaded ring 322 having a trocar seal 358 at its proximal end, as shown in FIG. 32.

Figure 27:
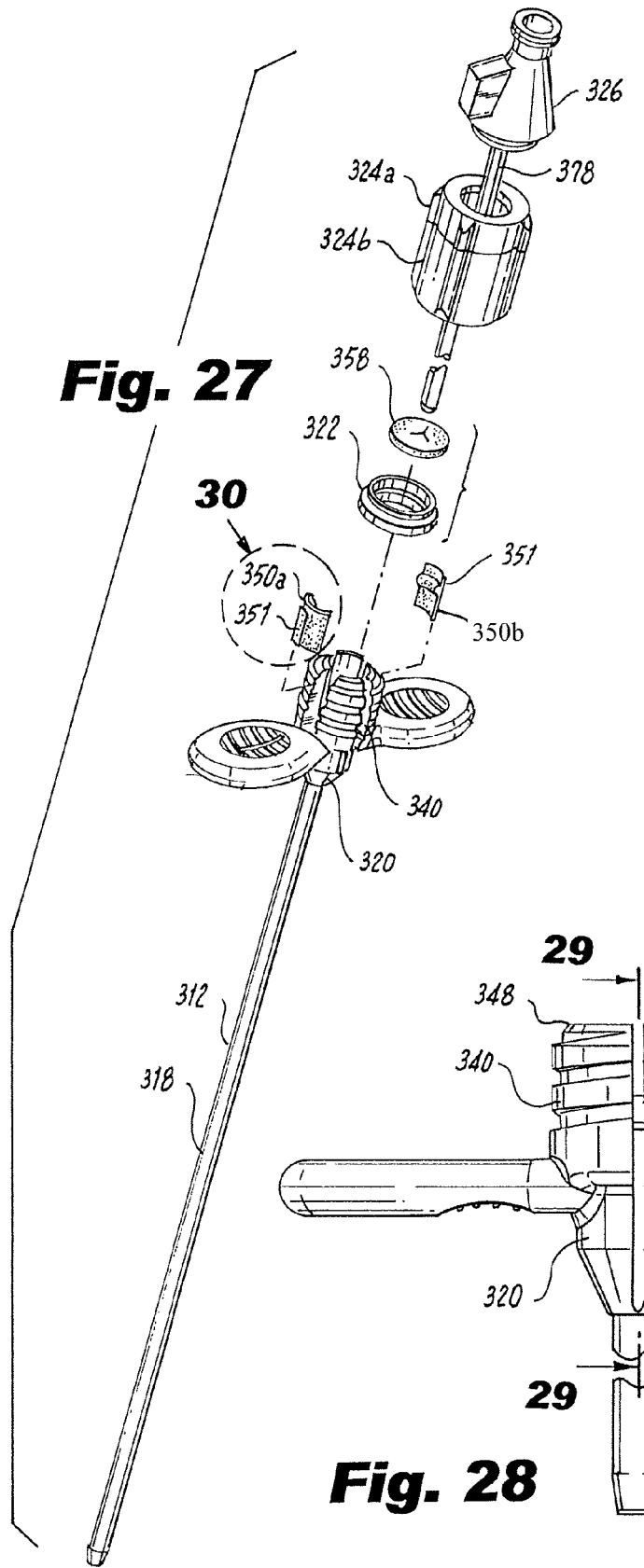
FIG. 27 is an exploded perspective view of a vascular introducer assembly constructed in accordance with another preferred embodiment of the subject invention with parts separated for ease of illustration.
Figure 28:
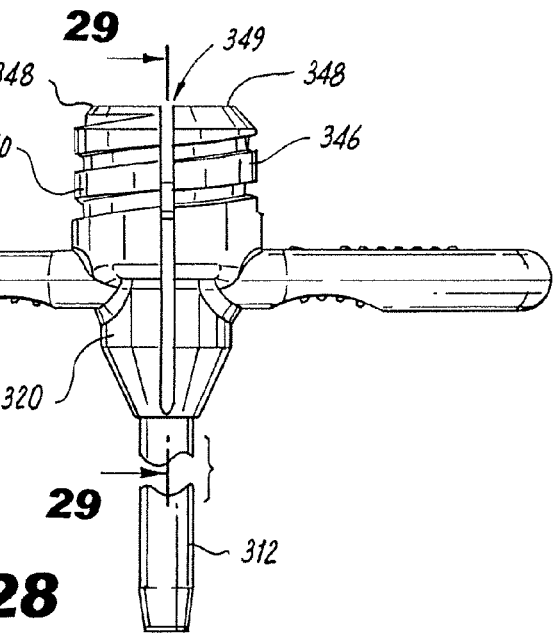
FIG. 28 is an enlarged front view of the hub portion of the vascular introducer assembly of FIG. 27, illustrating the larger diameter proximal end portion of the hub portion, among other things.

Threaded ring 322 is approximately the same diameter as proximal end portion 340. As shown in FIG. 27, sealing half-pipes 350a and 350b are inserted in axial bore 342b of proximal end portion 340 before threaded ring 322 is seated thereon. Proximal end portion 340 is of a larger diameter than in previous embodiments and includes a funnel-like opening in axial bore 342b, as shown in FIG. 29. Proximal end portion 340 also includes four axial slots 349 defining four axial projections 348 making up the proximal end portion 340 to enhance the range of radially inward movement, among other things.

As shown in FIG. 33, threaded ring 322 includes threads on its exterior that can match with threads 346 on proximal end portion 340. This feature allows the combination of threaded ring 322 and proximal end portion 340 to be simultaneously engaged with threads 368 defined on the interior surface of locking collar 324, as can be best viewed in FIGS. 36-40.

In this embodiment, locking collar 324 is splittable and defines a proximal end portion 324a and a distal end portion 324b, as shown in FIGS. 34 and 35. Proximal end portion 324a, which is connected with dilator handle 326, and a distal end portion 324b, which includes threads 368 defined on its interior surface. Proximal portion 324a of collar 324 can be separated from distal portion 324b with dilator handle 326 attached thereto. Distal portion 324b can be threaded onto threaded ring 322 and proximal end portion 340 of hub 320 without proximal portion 324a.

Figure 36:
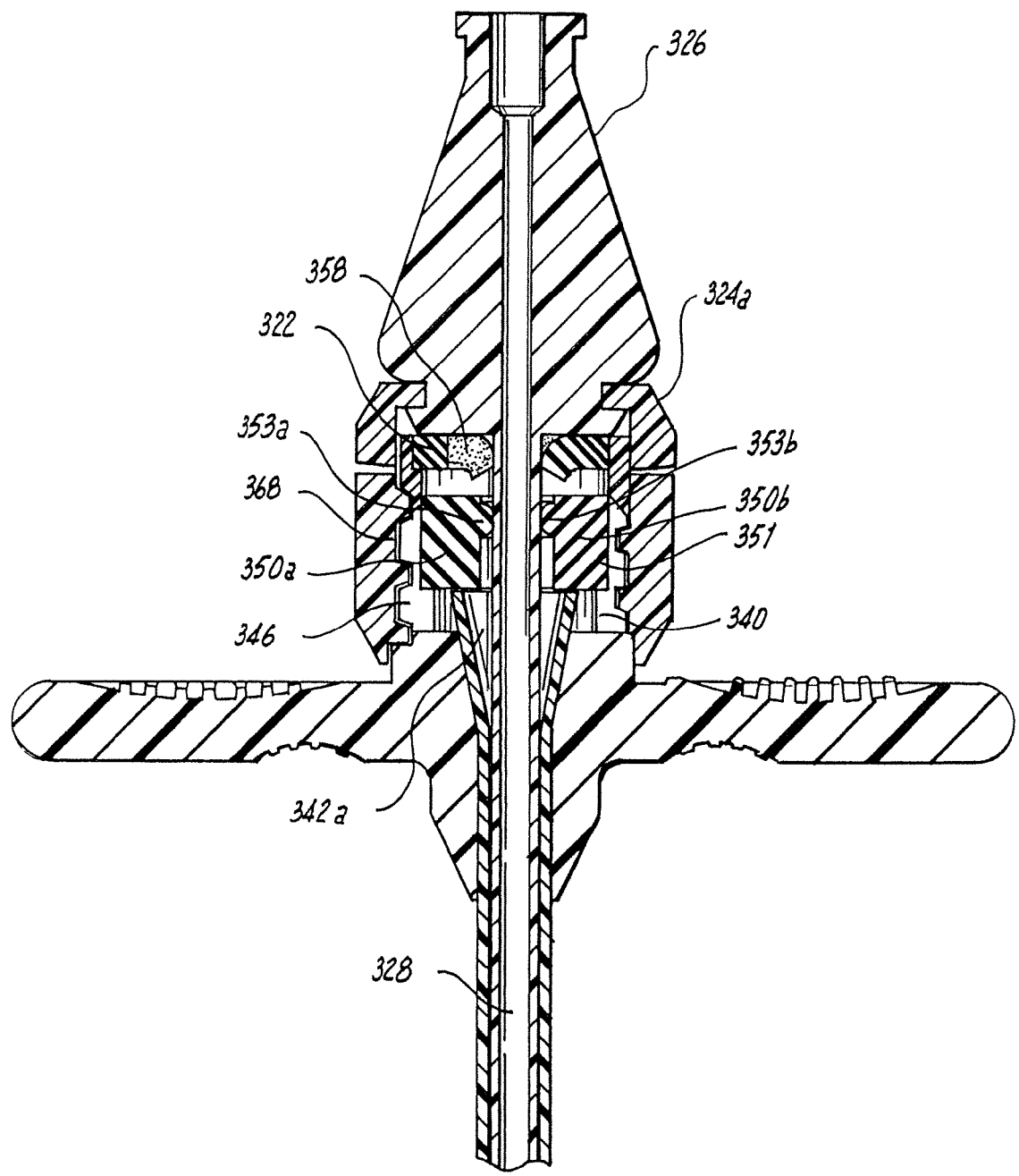
FIG. 36 is a cross sectional view of the hub portion of the vascular introducer of FIG. 27, wherein the dilator handle is mounted on the non-threaded portion of the locking collar, and the threaded portion of the locking collar is fully threaded onto the proximal end portion of the hub portion and over the annular member with the trocar seal, among other things.
Figure 37:
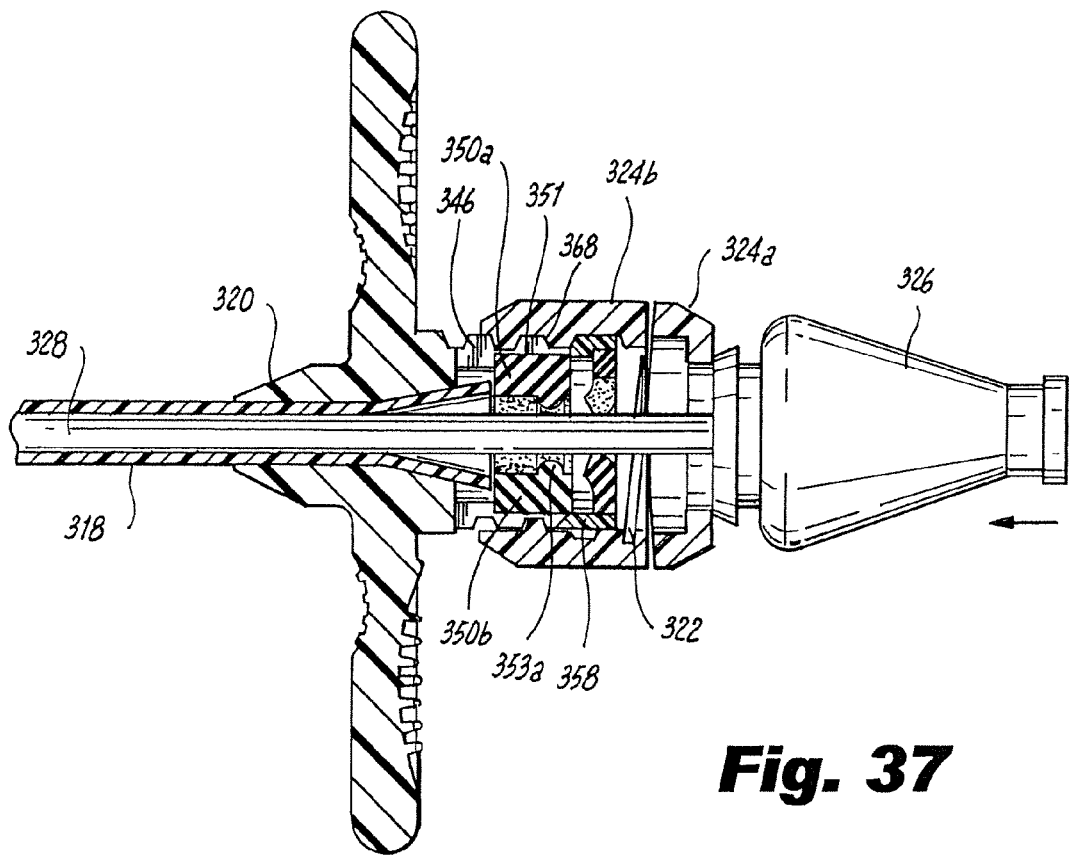
FIG. 37 is a partial cross sectional view of the hub portion of the vascular introducer of FIG. 27, wherein the dilator handle is mounted on the non-threaded portion of the locking collar, and the threaded portion of the locking collar is de-threaded on the proximal end portion of the hub portion and radially inward pressure on the annular seal is not applied, among other things.
Figure 38:
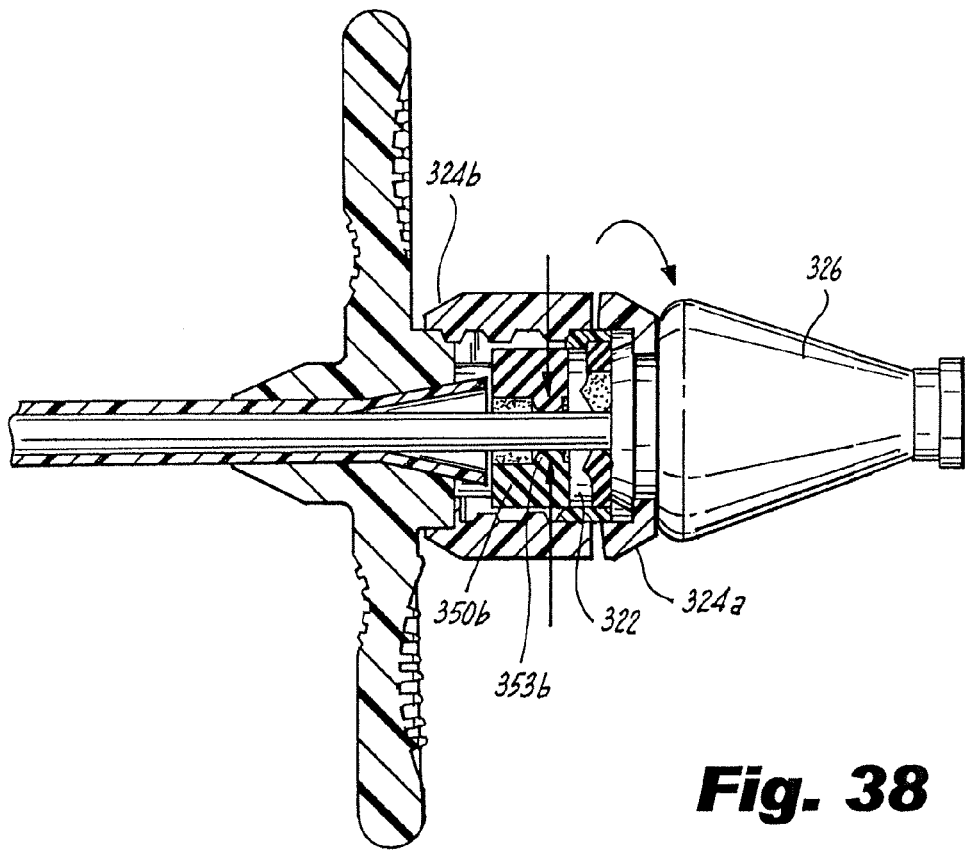
FIG. 38 is a partial cross sectional view of the hub portion of the vascular introducer of FIG. 27, wherein the dilator handle is mounted on the non-threaded portion of the locking collar, and as illustrated by the arrows, radially inward pressure on the annular seal is applied by the threaded portion of the locking collar being fully threaded onto the proximal end portion of the hub portion, among other things.

In use, threading collar 324 on threaded ring 322 and proximal end portion 340 applies a crimping action to sealing tube 350 therein, as can be best viewed in FIGS. 36 and 38. By being secured against proximal end portion 340, threaded ring 322 bears down on proximal end portion 340 when locking collar 324 is threaded on proximal end portion 340. This results in the radially inward movement of axial projections 348 of proximal end portion 340 causing inner rings 353a and 353b of seal 350 to contact dilator 328. The contact between rings 353a and 353b and dilator 328 forms a seal that prevents blood flow from exiting proximally through introducer 310. The crimping action can be released by de-threading collar 324 on proximal end portion 340, as shown in FIG. 37.

Thus, in this embodiment, collar 324 generally serves as both a sealing cap and a locking collar for dilator 328 and dilator handle 326, in that threading or de-threading collar 324 either seals or releases the seal created by cylindrical seal 350 and inner half rings 353a and 353b, among other things. Furthermore, as shown in FIG. 39-40, distal end portion 324b of collar 324 can actuate the crimping action without proximal end portion 324a.

Figure 39:
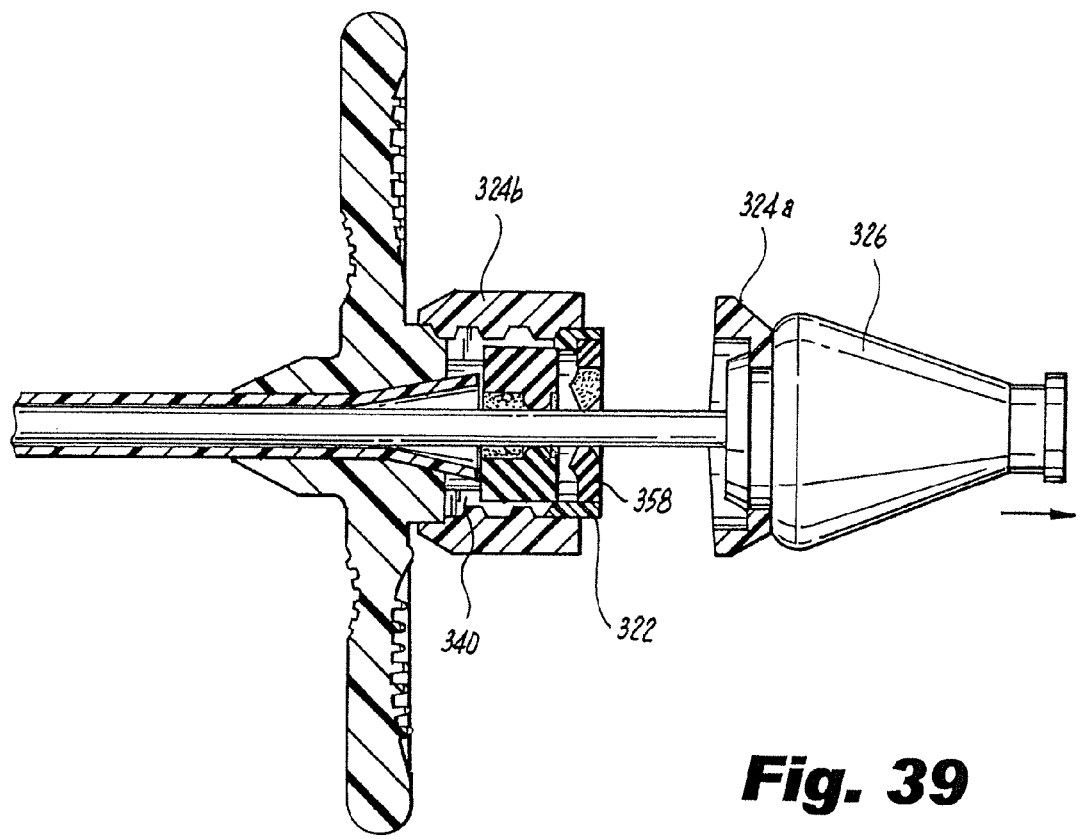
FIG. 39 is a partial cross sectional view of the hub portion of the vascular introducer of FIG. 27, illustrating the manner in which the locking collar can be separated to remove the dilator without removing the annular member with the trocar seal or de-threading the threaded portion of the locking collar from the proximal end portion of the hub portion, which remain in place to maintain the hemostatic valve in the closed position, among other things.

As can be viewed in FIG. 39, dilator handle 326 and dilator 328 may be removed from assembly 310 by separating proximal portion 324a of from distal portion 324b of locking collar 324. Distal end portion 324b of collar 324 can remain secured on proximal end portion 340 as a functioning actuator for the seal in proximal end portion 340 provided dilator 328 remains within introducer 310. If dilator 328 is separated from introducer 310, threaded ring 322 with trocar seal 358 remains in place adjacent proximal end portion 340 of hub 320 to prevent blood from escaping introducer 310, as shown clearly in FIGS. 39-40.

Figure 40:
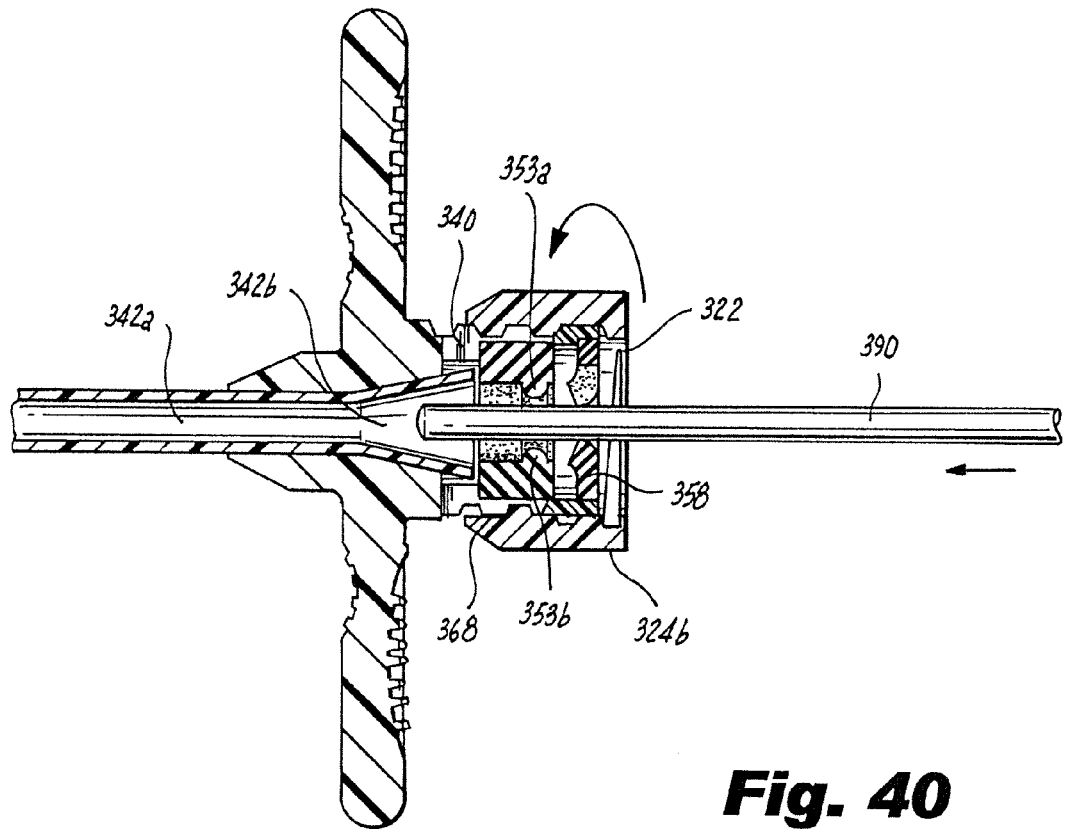
FIG. 40 is a partial cross sectional view of the hub portion of the vascular introducer of FIG. 27, illustrating the manner in which the threaded portion of the locking collar can actuate the hemostatic valve so that the valve can alternate between an open and closed position and an endocardial lead being inserted through the trocar in the annular member which remains in place on the proximal end portion.

Also, as shown in FIG. 40, introducer 310 can be used to insert devices or equipment intravenously through lumen 130, such as an endocardial lead 390, by de-threading distal collar portion 324b along proximal end portion 340 and threaded ring 322, which releases the crimping action on proximal end portion 340, but allows devices to be inserted through trocar seal 358 and the larger diameter proximal end portion 340.

FIGS. 41-46 and 47-51 illustrate further embodiments of vascular introducers in accordance with the invention, and more particularly to seal arrangements thereof. With reference to the embodiment of FIGS. 41-46, a vascular introducer in accordance with the invention is designated generally by reference numeral 4110. The vascular introducer 4110 includes a proximal hub portion 4112 of generally cylindrical configuration, which includes a central bore 4115 (see FIG. 42, for example) and a pair of radially extending diametrically opposed handle portions 4112a, 4112b. The central hub portion 4112 of vascular introducer 4110 has diametrically opposed parting lines 4114a, 4114b, (see FIG. 46, for example) for splitting the hub portion 4112 to facilitate its removal from a surgical site following placement of a lead or catheter therewith, similar to the splitting illustrated in FIG. 12.

An elongated tubular sheath 4116 extends distally from the hub portion 4112 to define an access path or lumen into a blood vessel. The sheath 4116 includes diametrically opposed lines of weakness (not visible in the drawings) which are aligned with the parting lines 4114a, 4114b of the hub portion 4112. These lines of weakness can be score lines, areas of thinned material thickness of another type, to facilitate splitting of the sheath 4116, enabling the sheath 4116 to be pealed-away from a surgical implement, such as a lead or catheter inserted therethrough. During the removal of the sheath 4116, the split hub portions will also be separated following placement of a lead, catheter or other implement. Those skilled in the art will readily appreciate that the length and/or diameter of the sheath 16 can vary depending upon application and intended use.

Figure 41:
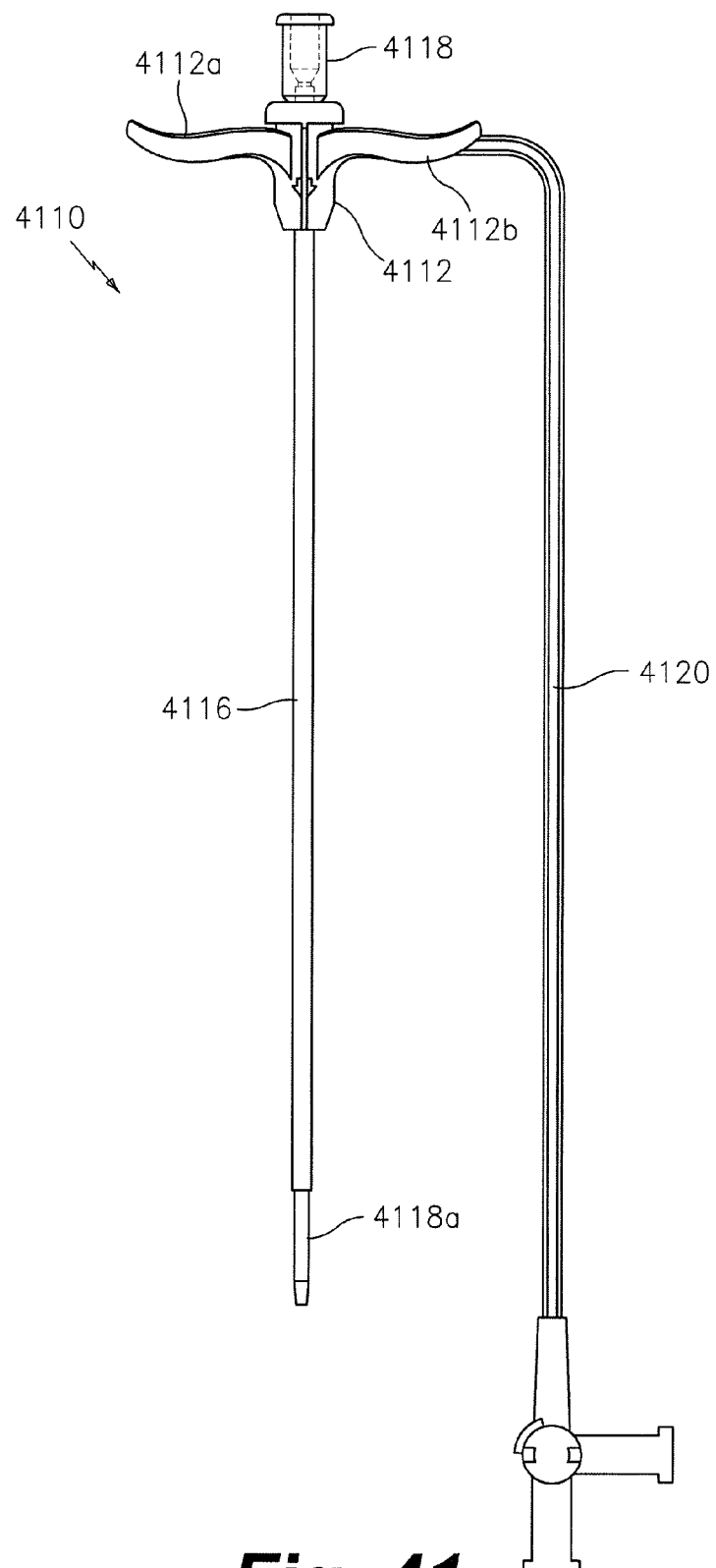
FIG. 41 is a side view of a vascular introducer constructed in accordance with a preferred embodiment of the subject invention, which is shown in conjunction with a ported dilator extended through the introducer and with a fluid delivery conduit operatively associated with a side port of the central hub portion of the introducer.

FIG. 41 further illustrates an elongated ported dilator 4118 that extends through the introducer 4110 and includes a tapered distal end portion 4118a to facilitate percutaneous introduction of the sheath 4116 into a blood vessel. The dilator 4118 preferably has a lumen for introduction of a guidewire, or for injection of a medicament, contrast solution or other substance. A fluid delivery conduit 4120 is operatively associated with a side port 4122 of the introducer hub portion 4112, as shown for example in FIG. 42. The fluid delivery conduit 4120 is adapted and configured to deliver fluid into the introducer 4110 to irrigate or flush out the sheath 4116 or for infusion or injection of a medicament, contrast solution or the like. Additionally, vacuum can be applied through the fluid delivery conduit 4120, if desired.

Figure 43:
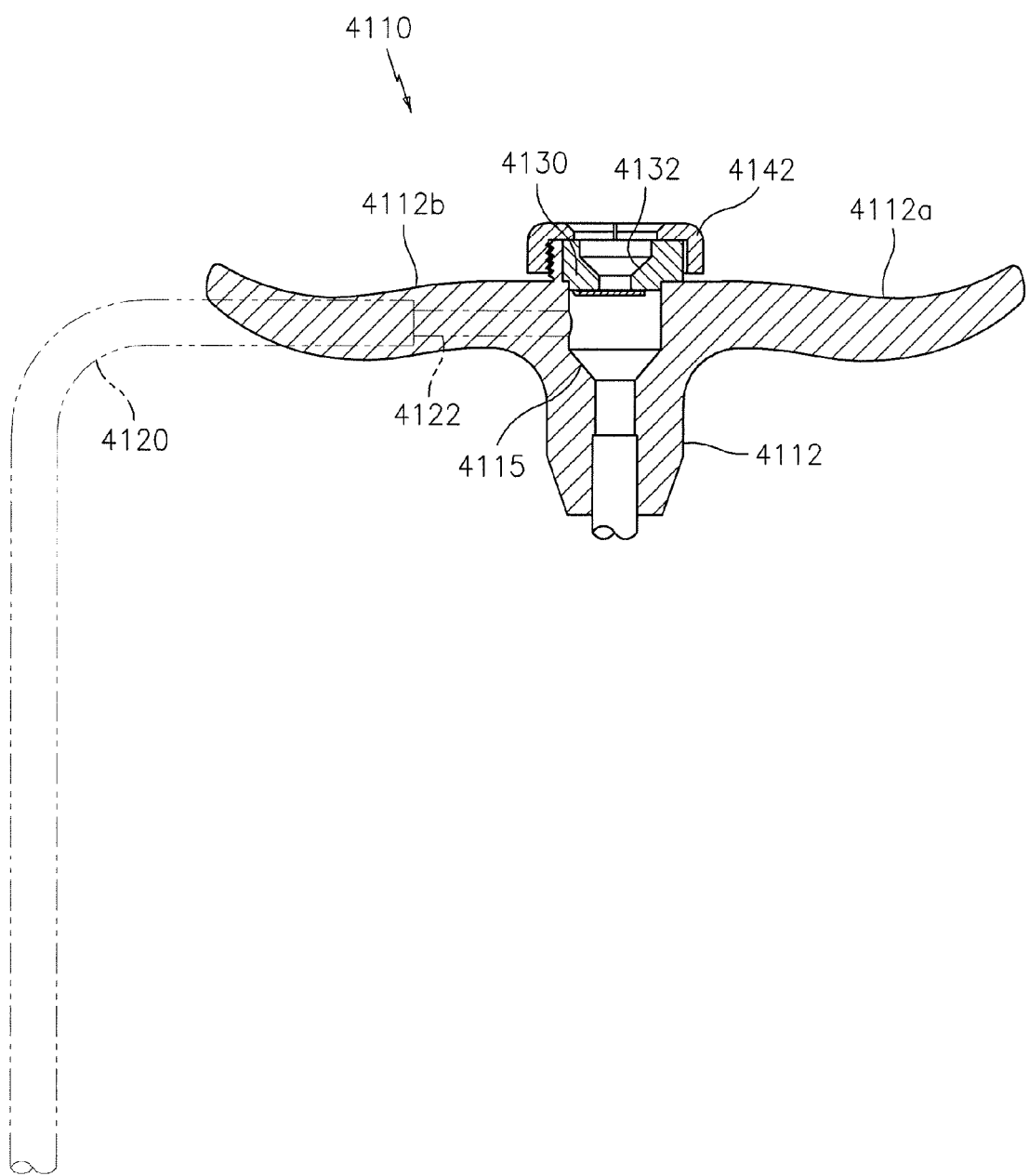
FIG. 43 is a cross-sectional view of the introducer hub portion rotated 180° from the position shown in FIG. 42 and depicted with the sealing flap of the hemostatic valve oriented in a closed position to block fluid egress or back flow of blood through the axial passage of the hemostatic valve.
Figure 44:
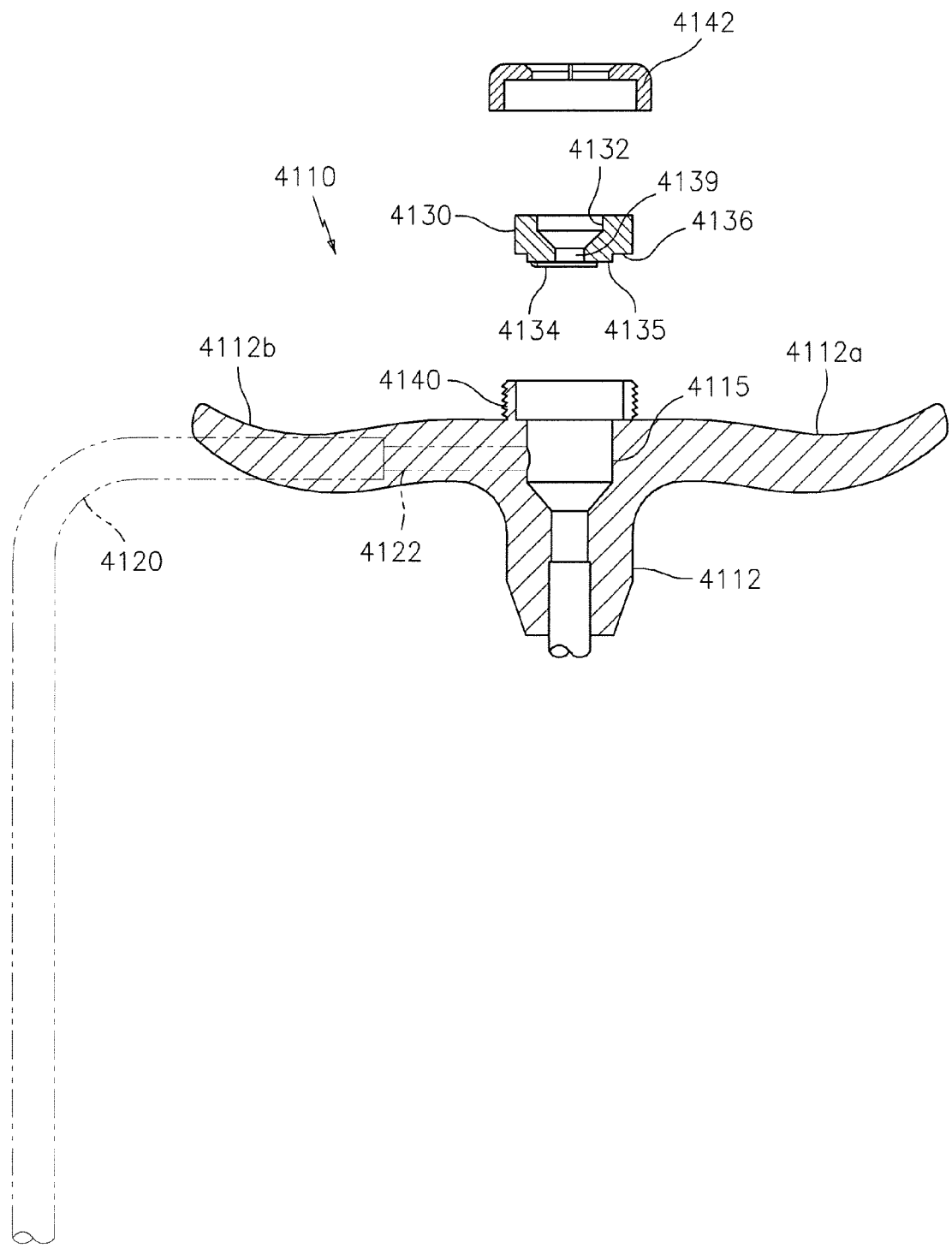
FIG. 44 is a side view of the introducer hub portion as shown in FIG. 43, with parts separated for ease of illustration, including the hemostatic valve and retaining collar.
Figure 45:
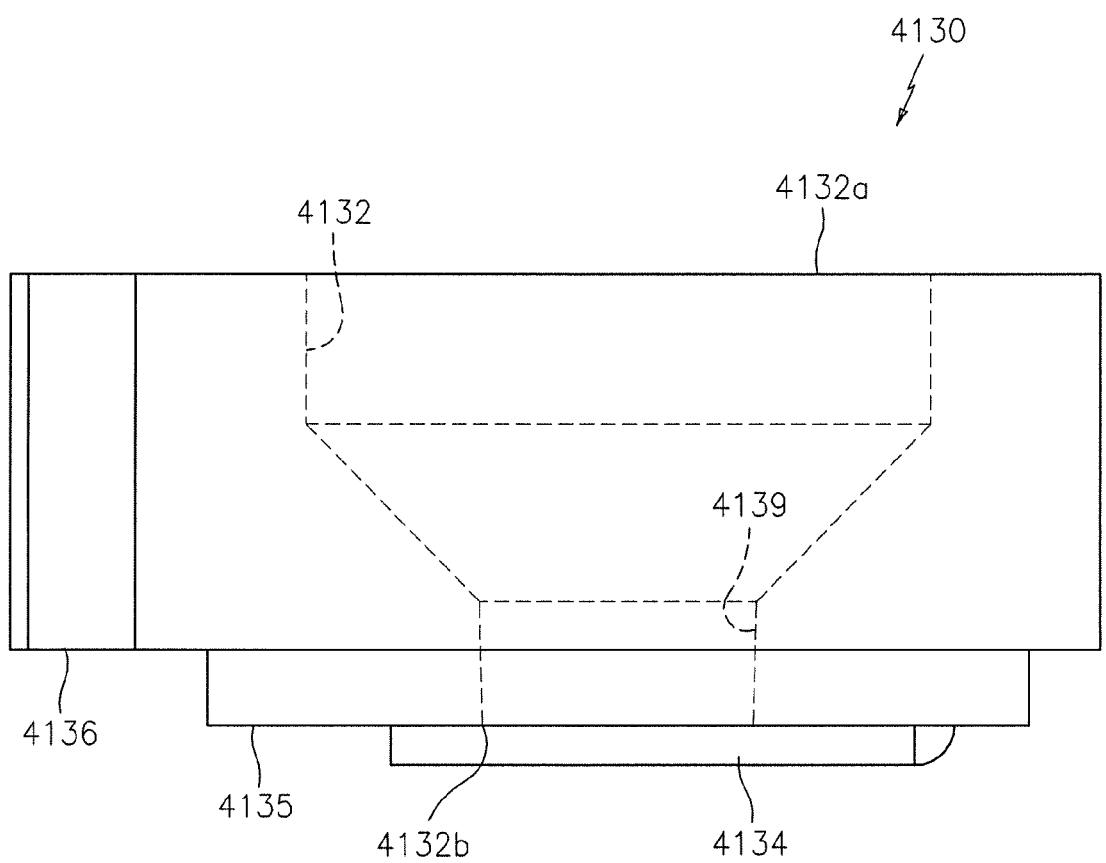
FIG. 45 is an enlarged side view of the hemostatic valve of the vascular introducer shown in FIGS. 41 through 44.

Referring particularly to FIGS. 43-45, the vascular introducer 4110 includes a hemostatic valve member 4130 supported within the interior bore 4115 of the central hub portion 4112 thereof. Additionally, the valve member 4130 is separately illustrated in FIG. 45 for increased clarity.

The valve member 4130 is preferably made of an elastomeric material, such as a silicone rubber. However, other suitable elastomeric materials can be used. The valve member 4130 includes an inwardly tapering axial passage 4132 having a proximal inlet end 4132a and a distal outlet end 4132b.

Figure 42:
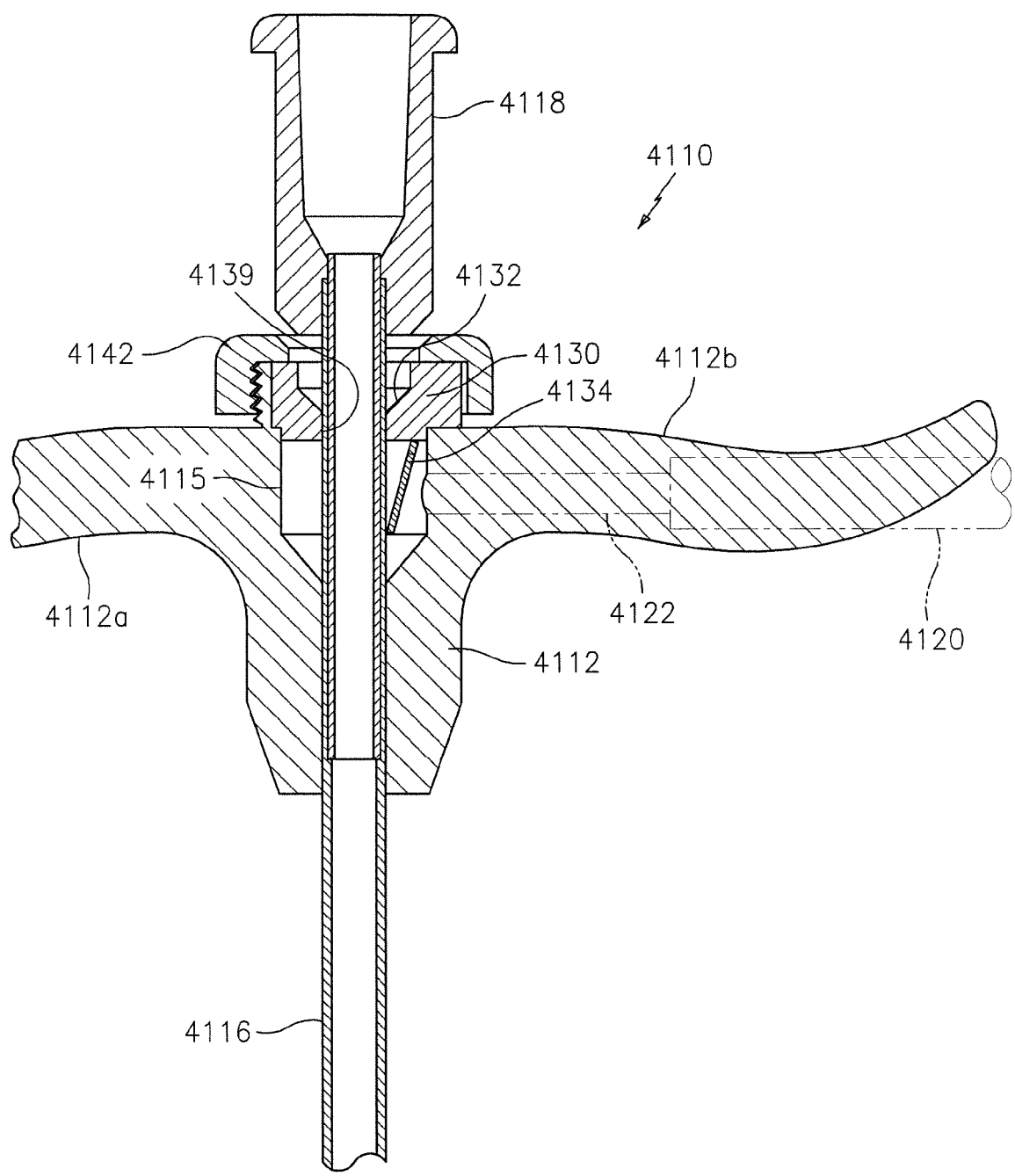
FIG. 42 is an enlarged cross-sectional view of the vascular introducer of FIG. 41 showing the open position of the sealing flap associated with the hemostatic valve disposed within the interior cavity of the central hub portion of the introducer.

A sealing flap 4134, which can have, for example a circular or ovoid shape, is operatively associated with the bottom surface portion 4135 of valve member 4130 for closing off and otherwise sealing the distal (lower) outlet end 4132b of the axial passage 4132. More particularly, the sealing flap 4134 is adapted and configured to move between an open position, as shown in FIG. 42, when the dilator 4118 or a device such as a pacemaker lead or catheter passes through the hub portion 4112 into the sheath 4116, and a closed or sealing position, which is shown in FIGS. 43-45, when the dilator or device is not present in the introducer 4110.

Figure 47:
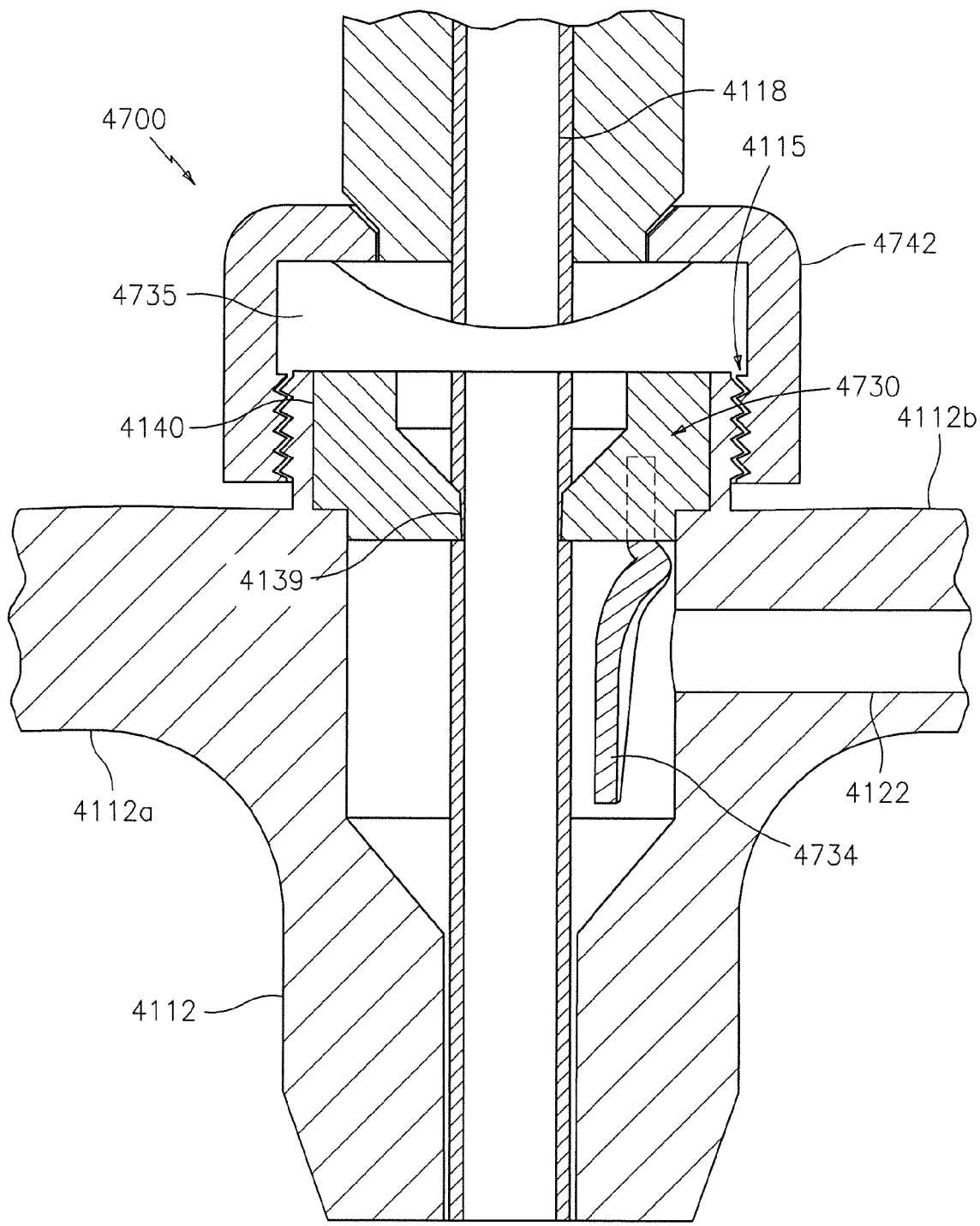
FIG. 47 is an enlarged cross-sectional view of another embodiment of a vascular introducer constructed in accordance with the subject invention, which includes an additional secondary proximal seal element.
Figure 48:
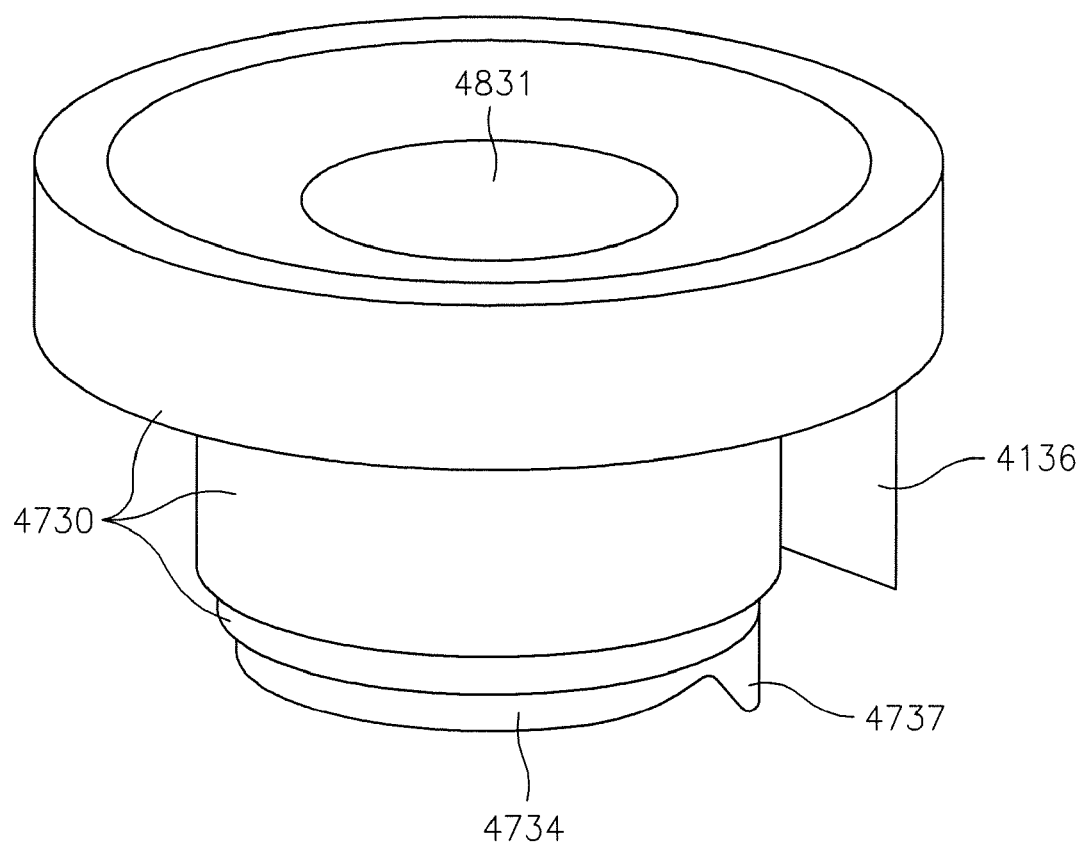
FIG. 48 is an isolated isometric view of the hemostatic seal and secondary seal of the vascular introducer of FIG. 47.

The sealing flap 4134 can have any shape necessary, but generally circular, ovoid or oblong shapes are particularly conceived. The sealing flap 4134 can be integrally formed with the valve member 4130, as by molding. In the alternative, the sealing flap 4134 can be formed separately from the valve member 4130 and attached thereto, such as by a suitable welding technique such as solvent, friction or ultrasonic welding, a suitable adhesive or by mechanical connection to the lower end surface portion 4135 of the valve member 4130. Alternatively still, as shown in FIG. 47, the sealing flap 4134 can be inserted into a receptacle formed in the main body of the valve member 4130.

Moreover, in any embodiment, the sealing flap 4134 can be connected to the main body of the valve member 4130 directly or by way of a hinge. Also, if so embodied, each of the valve member 4130 and the sealing flap 4134 can be in contact with or respectively attached to a third intermediate element, such as a structural member including but not limited to the hub 4112 itself, an intermediate structural member or hinge.

Figure 46:
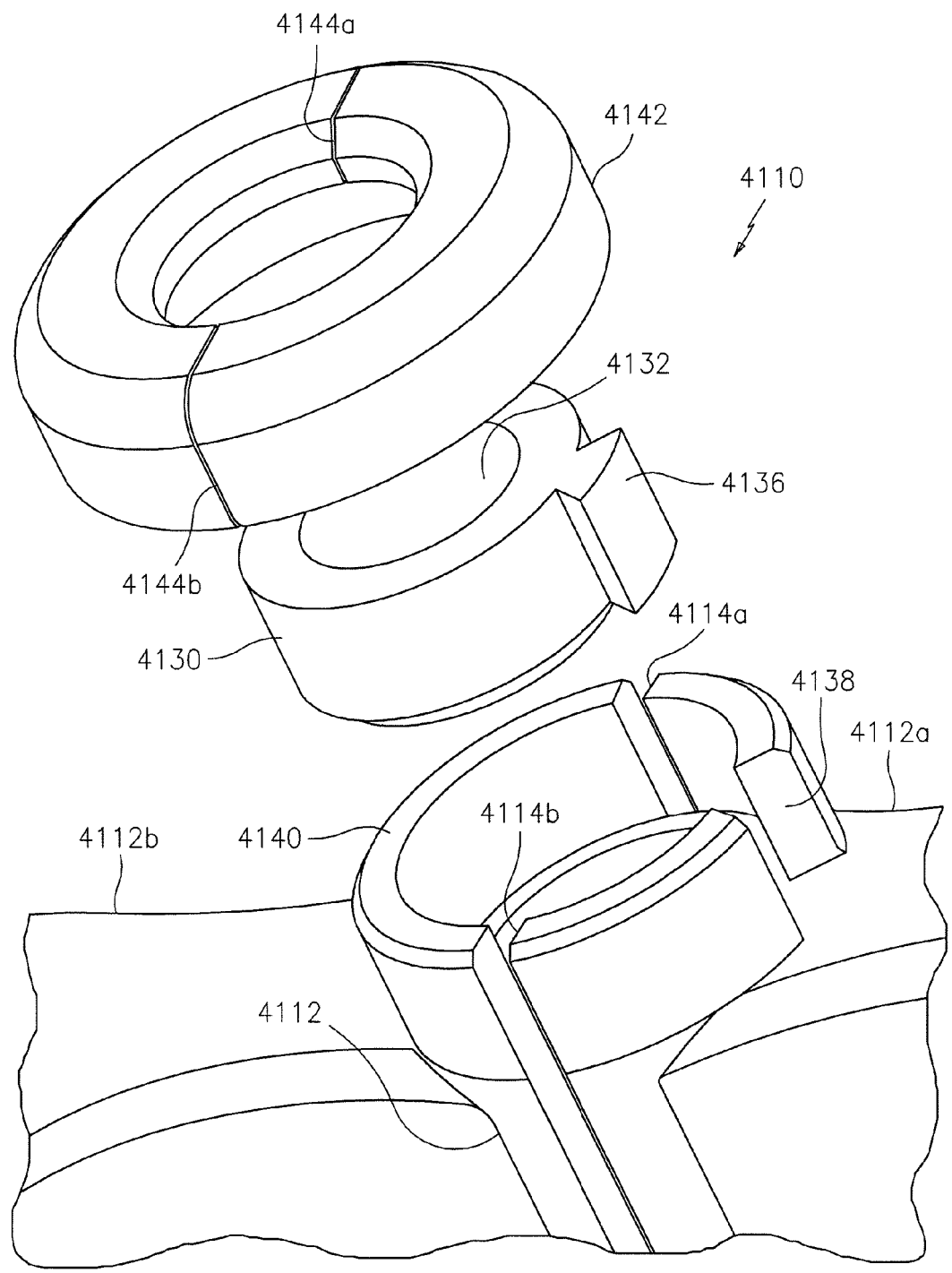
FIG. 46 is an enlarged exploded perspective view of the hub portion of the vascular introducer shown in FIG. 41.

As best seen in FIG. 46, the valve member 4130 can be embodied to include a key 4136, dimensioned and configured for reception by and engagement with a corresponding recess 4138 defined in the upper wall 4140 of the central hub portion 4112 of vascular introducer 4110. The valve member 4130 can be provided with a parting line (not visible in the drawing), which is diametrically opposed to the key 4136 and is displaced by 90° from the parting lines 4114a, 4114b of central hub portion 4112, when assembled. When the hub portion 4112 is split along the parting lines 4114a, 4114b for removal, the valve member 4130 will part along its respective parting line, thereby facilitating separation of the vascular introducer 4110 from a lead or catheter passing therethrough. Moreover, a retaining collar 4142 is provided for capturing the valve member 4130 within the interior bore 4115 of the central hub portion 4112. The retaining collar 4142 can be configured to be splittable, and to include diametrically opposed parting lines 4144a, 4144b that align with the parting lines 4114a, 4114b of central hub portion 4112.

Referring now to the embodiments of FIGS. 47-51, there is illustrated another embodiment of the vascular introducer designated generally by reference numeral 4700. Vascular introducer 4700 is similar to vascular introducer 4110. However, among other distinctions, the vascular introducer includes a second seal member 4735 formed from a flexible material and located proximal to a lower valve member 4730. The lower valve member 4730 is similar in configuration to the valve member 4130, except as set forth below, but alternatively can be identical to the valve member 4130. The second seal member 4735 is arranged below the retaining collar 4142, between the upper wall 4140 of the hub 4112 and the retaining collar 4142. In this embodiment, the retaining collar 4142 is deeper than that illustrated in connection with the embodiments of FIGS. 41-46 in order to accommodate the second sealing element 4735.

The lower valve member 4130 and the sealing member 4735 can be integrally formed, such as by molding, or alternatively can be separately formed. If formed separately, these elements can be mutually joined by a suitable technique, or simply inserted separately into the bore 4115 or otherwise applied in the proximal region of the vascular introducer 4700.

The sealing member 4735 can be configured in any a variety of advantageous morphologies. As illustrated, the sealing member 4735 includes a central aperture 4831 (FIG. 48), which is expanded when an instrument, such as the dilator 4118 is inserted therethrough to provide a reliable seal therebetween. Seal tightness that is effective but does not severely impact passage of surgical instruments is preferred. The sealing member 4735 can be provided simply as an O-ring, a cuspid valve (e.g., bicuspid, tricuspid or quadricuspid) or as a septum-type valve with an internal circular apertures slits formed therein with any of a number of pre-formed diameters or lengths in a relaxed state, each of which can expand upon insertion of an instrument. Alternatively, the sealing member 4725 can be embodied as a pierceable and resealable membrane having no defined aperture defined therein, which is advantageous for use with instruments having very small diameters, such as needles and the like. Moreover, when provided in a kit, a plurality of sealing members 4735 can be supplied, in order to optimally seal against a variety of instruments which may be inserted therethrough. In such an instance, if a particular instrument is to be used—for example, one having a relatively large diameter—then the appropriate sealing member 4735 can be selected and placed in position, with the retaining collar 4742 placed thereover.

As with the lower valve member 4730, the second seal member 4735 can be embodied so as to be readily broken apart along one or more parting lines to facilitate separation of the vascular introducer 4700 from a lead or catheter following emplacement thereof.

Figure 49:
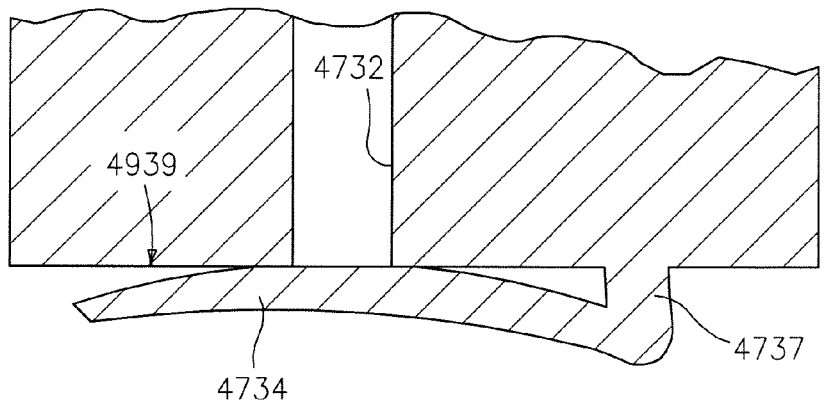
FIG. 49 is a side view of one configuration for the lower sealing flap and seat therefor of the hemostatic seal of the vascular introducer of FIG. 47, where a sealing flap having a convexly contoured upper surface and a substantially flat valve seat therefor are provided.
Figure 50:
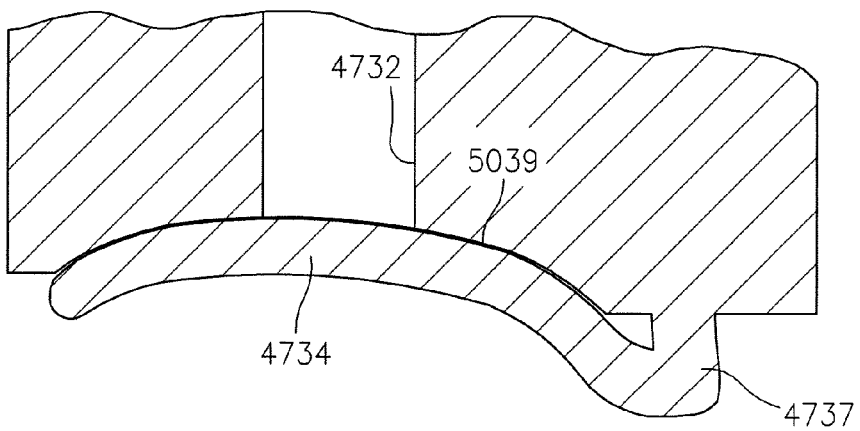
FIG. 50 is a side view of a another configuration for the lower sealing flap and seat therefor of the hemostatic seal of the vascular introducer of FIG. 47, where a sealing flap having a convexly contoured upper surface and a complementary concave valve seat therefor are provided.
Figure 51:
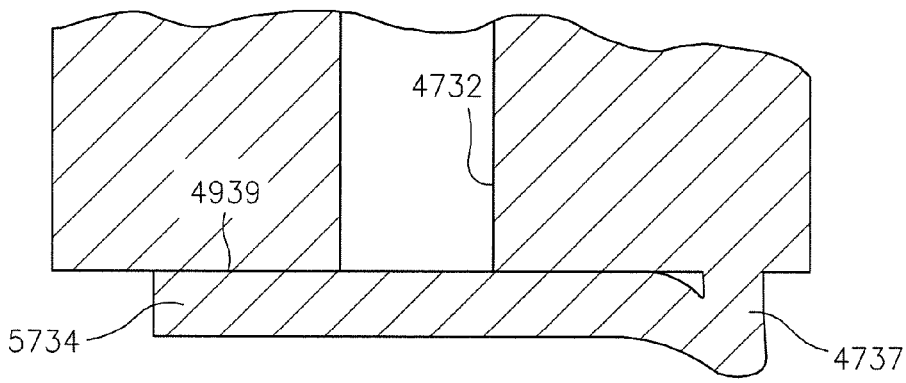
FIG. 51 is a side view of a third configuration for the lower sealing flap and seat therefor of the hemostatic seal of the vascular introducer of FIG. 47, where a sealing flap and valve seat therefor are substantially planar.

As shown, for example in FIG. 49, a sealing flap 4734 can be provided with a proximal convexity, which in combination with a substantially flat seat 4939, can thereby occlude the inner channel 4732 of the valve member 4730 in the absence of an instrument inserted therethrough. Alternatively, the seat for the sealing flap 4734 can be concave itself, complementing the curvature of the sealing flap 4734, as illustrated in FIG. 50 with the seat 5039 and sealing flap 4734. The embodiment of FIG. 51 illustrates another permutation, including a substantially planar sealing flap 5734, and a substantially planar seat 4939 therefor.

However, each of the sealing flaps of the embodiments of FIGS. 47-51, and as can be optionally provided in the embodiment of FIGS. 41-46, includes a curved hinge element 4737, to enhance sealing by urging the sealing flap 4734 toward its respective seat. The configuration of the hinge 4737 in a preferred embodiment, is molded such that the resting position of the sealing flap (e.g. sealing flap 4734) is in the closed position, or at a point proximal the closed position such that a constant elastic force is exerted by the hinge 4737 on the sealing flap (e.g. sealing flap 4734), urging the sealing flap against its seat in the absence of other external forces.

As illustrated in the embodiment of FIGS. 41-46, the hinge can simply be a small piece of connecting material, and as illustrated in the embodiment of FIGS. 47-51, the hinge can be more robust, having an inherent deformation to urge the sealing flap into the closed position. Naturally, the hinge can be integrally formed with the sealing flap and/or the body of the valve member 4730, such as by molding. Alternatively, the hinge can be integrally formed with one of the sealing flap and/or the body of the valve member 4730, and then connected to the other in a suitable manner. Alternatively still, a separately formed hinge can be connected with the valve body and the flap 4734.

Advantageously, in the absence of contrary influences, such as during the insertion of an instrument through the axial passage 4132 of the hemostatic seal 4130 or the hemostatic seal 4730, the natural curvature of the hinge 4737 helps urge the sealing flap 4734 into a closed position. Accordingly, undesirable flow of blood from the puncture through the vascular introducer is inhibited. The sealing effect is even more pronounced when a vacuum is applied to the proximal side of sealing flap 4734, for example through the side port 4122, which urges the sealing flap 4734 into close contact with its seat, thereby enhancing the seal therebetween. A tight seal can thus be induced during a procedure when necessary, in order to inhibit blood loss or air embolism, by applying a vacuum through the side port 4122.

In the illustrated embodiments of FIGS. 41-51, the respective vascular introducers 4110, 4700 include a proximal hub portion 4112, having a central bore 4115 formed therein. The hemostatic valves 4130 and 4730 are inserted therein, and can be held in the desired rotational position by way of a key element 4136 provided thereon. In the embodiment of FIGS. 41-46, the retaining collar 4142 is threaded or press-fit onto the hub 4112, or attached thereto in another manner, and thereby maintains the hemostatic valve 4130 within the central bore 4115 of the introducer 4110. In the embodiment of FIGS. 47-51, a secondary seal 4735 separate from or integrally formed with the hemostatic valve 4730 is also provided. As illustrated, this secondary seal 4735 may be provided such that it rests on the proximal end of the hub upper wall 4140, between the hub upper wall 4140 and the retaining collar 4142. As described above, the retaining collar 4142 may need to be taller than that for the embodiment of FIGS. 41-46, in order to provide sufficient space for the secondary sealing member 4735. As mentioned above, the seal 4735 can be of any variety of suitable types including but not limited to an O-ring, a cuspid valve or as a septum-type valve, for example.

Alternatively, the bore 4115 of the introducer 4700 can be enlarged to directly accommodate the second seal member 4735. However, with the arrangement illustrated in the embodiment of FIG. 47, advantageously the hub 4112 need not be reconfigured in order to provide additional sealing capability, there reducing tooling cost.

Depending on the precise implementation, it may be desirable to choose a proximal secondary sealing element 4735 based on the type or size of the instrument to be inserted therethrough. Accordingly, having a simple, intuitive engagement between the hub 4112 and the retaining collar 4142 may be beneficial. The retaining collar 4142 can be secured to the hub upper wall 4140 by way of a suitable thread arrangement, or alternatively by a snap fit, friction fit, interference fit, bayonet-type latch or other suitable arrangement.

When an instrument is inserted through either of the vascular introducers illustrated in FIGS. 41-51, the sealing flap, which is ordinarily in a closed state, is urged downward to an open position as the instrument passes by. The sealing flap remains in this condition until the instrument is removed.

Moreover, while the sealing flaps 4134, 4734 seal the passageway 4132 when in the closed position, they are not capable of sealing the passageway when in the open position. Accordingly, an inner annular distal portion 4139 of the valve member 4130 can be sized so that it sealingly contacts the outer surface of an instrument inserted through the passageway 4132, as shown in FIGS. 42 and 47. In the embodiment of FIGS. 47-51, therefore, dual seals provide redundancy and improved seal effectiveness in use, combining this distal annular seal 4139 with the second, more proximal seal 4735.

The methods and systems of the present invention, as described above and shown in the drawings, provide for a vascular introducer with superior properties, minimizing undesirable blood loss through the vascular introducer during procedures. It will be apparent to those skilled in the art that various modifications and variations can be made in the device and method of the present invention without departing from the spirit or scope of the invention. Thus, it is intended that the present invention include modifications and variations that are within the scope of the appended claims and their equivalents.

What is claimed is:

1. A vascular introducer comprising:
   a) a proximal hub portion which defines an interior bore and an outer engagement surface, the interior bore configured to receive a dilator having a proximal end and a distal end, the outer engagement surface configured to engage a locking collar coupled to the dilator;
   b) an elongated sheath extending distally from the hub portion and defining a lumen in communication with the interior bore of the hub portion, the lumen configured to receive the dilator; and
   c) a hemostatic valve disposed within the bore of the proximal hub portion and having a passage extending therethrough, the hemostatic valve including a sealing flap and a distal end wall, the sealing flap having a convex portion movable between an open position relative to the passage and a closed position relative to the passage, the distal end wall defining a concave seat opposite the sealing flap, wherein a majority surface portion of the concave seat and a majority surface portion of the convex portion of the sealing flap are configured to complement and arcuately align with one another to enhance a seal formed therebetween in the closed position.

2. The vascular introducer of claim 1, wherein the hemostatic valve includes a hinge, and the convex proximal of the sealing flap is operatively disposed adjacent the hinge.

3. The vascular introducer of claim 2, further comprising a second seal element provided within the interior bore of the hub portion proximal of the hemostatic valve, the second seal element also having a passage extending therethrough and configured to sealingly engage an outer surface of a surgical implement inserted therethrough.

4. The vascular introducer of claim 3, wherein the hemostatic valve and the second seal element are integrally formed with one another.

5. The vascular introducer of claim 1, wherein the sealing flap is attached to the hemostatic valve with a hinge element integrally formed with the sealing flap.

6. The vascular introducer of claim 5, wherein the hinge element is formed with a predefined morphology to urge the sealing flap into the closed position.

7. The vascular introducer of claim 1, wherein the sealing flap is arranged on a distal portion of the hemostatic valve.

8. The vascular introducer of claim 1, wherein the sealing flap is integrally formed with the hemostatic valve.

9. The vascular introducer of claim 1, wherein the sealing flap is separately formed from the hemostatic valve and attached thereto.

10. A vascular introducer system, comprising:
    (a) a proximal hub portion which defines an interior bore and an outer engagement surface;
    (b) an elongated sheath extending distally from the hub portion and defining a lumen in communication with the interior bore of the hub portion;
    c) a hemostatic valve operably disposed within the bore of the proximal hub portion and defining a passage extending therethrough, the hemostatic valve including a sealing flap and a distal end wall, the sealing flap having a convex portion movable between an open position relative to the passage and a closed position relative to the passage, the distal end wall defining a concave seat opposite the sealing flap, wherein a majority surface portion of the concave seat and a majority surface portion of the convex portion of the sealing flap are configured to complement and arcuately align with one another to enhance a seal formed therebetween in the closed position;
    d) a dilator having a proximal end and a distal tapered end configured to enter a blood vessel, the dilator longitudinally translatable through the lumen of the elongated sheath and the interior bore of the hub portion; and
    e) a locking collar attached to the proximal end of the dilator and configured to engage the outer engagement surface of the proximal hub portion.

11. A system according to claim 10, wherein the system is configurable to a second configuration in which the dilator and locking collar are seperated from the proximal hub portion, and the sealing flap is disposed in the closed position relative to the passage.

12. A system according to claim 11, wherein the passage of the hemostatic valve is fluidly isolated from the lumen of the elongated sheath in the second configuration.

13. A system according to claim 11, wherein the locking collar is adjustable to disengage the outer engagement surface of the proximal hub portion to facilitate removal of the dilator and locking collar from the proximal hub portion.

14. A vascular introducer system according to claim 10, wherein the system is configurable to a first configuration in which the locking collar is engaged with the outer engagement surface of the proximal hub portion, the sealing flap is disposed in the open position relative to the passage, and the dilator extends through the proximal hub portion, the hemostatic valve, and the elongated sheath.

15. A system according to claim 14, wherein the dilator is longitudinally fixed relative to the proximal hub portion in the first configuration.

16. A vascular introducer comprising:
   a) a proximal hub portion which defines an interior bore and an outer engagement surface, the interior bore configured to receive a dilator having a proximal end and a distal end, the outer engagement surface configured to engage a locking collar coupled to the proximal end of the dilator;
   b) an elongated sheath extending distally from the hub portion and having a lumen in communication with the interior bore of the hub portion;
   c) a hemostatic valve disposed within the bore of the hub portion and having a passage extending therethrough, the hemostatic valve including a convexly contoured sealing flap and a distal end wall, the sealing flap movable between an open position relative to the passage and a closed position relative to the passage, the distal end wall defining a concave seat opposite the sealing flap, wherein a majority surface portion of the concave seat and a majority surface portion of the sealing flap are configured to complement and arcuately align with one another to enhance a seal formed therebetween in the closed position; and
   d) a seal member located proximal to the hemostatic valve.

17. The vascular introducer of claim 16, wherein the seal member is an annular sealing member.

18. The vascular introducer of claim 16, wherein the seal member is adapted and configured to seal against an instrument inserted therethrough.

19. The vascular introducer of claim 16, wherein the seal member is a radially-expandable valve member configured to adjustably seal against different diameter instruments inserted therethrough.

20. The vascular introducer of claim 16, wherein the seal member is integrally formed with the hemostatic valve.

21. The vascular introducer of claim 16, further comprising a hinge element provided between the sealing flap and a body of the hemostatic valve.

22. The vascular introducer of claim 16, wherein the sealing flap is secured directly to a body of the hemostatic valve.

23. A method of inserting a vascularly introduced medical device, comprising the steps of:
   (a) providing a vascular introducer comprising:
      i) a proximal hub portion which defines an interior bore and an outer engagement surface, the interior bore configured to receive a dilator having a proximal end and a distal end, the outer engagement surface configured to engage a locking collar coupled to the proximal end of the dilator;
      ii) an elongated sheath configured to receive the dilator and extending distally from the hub portion, the sheath having a lumen in communication with the interior bore of the hub portion; and
      iii) a hemostatic valve disposed within the bore of the hub portion and having a passage extending therethrough, the hemostatic valve including a sealing flap and a distal end wall, the sealing flap having a convex portion movable between an open position relative to the passage and a closed position relative to the passage, the distal end wall defining a concave seat opposite the sealing flap, wherein a majority surface portion of the concave seat and a majority surface portion of the convex portion of the sealing flap are configured to complement and arcuately align with one another to enhance a seal formed therebetween in the closed position;
   (b) inserting a needle into a blood vessel of a patient in a desired location;
   (c) inserting a guidewire through the needle cannula to a desired depth;
   (d) withdrawing the needle from the desired location, leaving the guidewire protruding through the blood vessel and skin of the patient;
   (e) threading the vascular introducer and dilator over the guide wire;
   (f) removing the dilator and guidewire, leaving the sheath of the introducer protruding through the skin into the blood vessel;
   (g) introducing the medical device into the sheath;
   (h) advancing the medical device to the desired location; and
   (i) removing the sheath, thereby leaving the medical device disposed within the blood vessel of the patient.

* * * * *